United States Patent
De Jong et al.

(10) Patent No.: US 11,667,902 B2
(45) Date of Patent: *Jun. 6, 2023

(54) LIPOLYTIC ENZYME VARIANTS

(71) Applicant: DSM IP ASSETS B.V., Heerlen (NL)

(72) Inventors: Rene Marcel De Jong, Echt (NL); Chantal Christis, Echt (NL); Neil Carr, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 190 days.

This patent is subject to a terminal disclaimer.

(21) Appl. No.: 17/109,759

(22) Filed: Dec. 2, 2020

(65) Prior Publication Data

US 2021/0087542 A1 Mar. 25, 2021

Related U.S. Application Data

(63) Continuation of application No. 16/471,121, filed as application No. PCT/EP2017/083526 on Dec. 19, 2017, now Pat. No. 10,889,807.

(30) Foreign Application Priority Data

Dec. 21, 2016 (EP) ..................................... 16205906
Feb. 21, 2017 (EP) ..................................... 17157061

(51) Int. Cl.
*C12N 9/20* (2006.01)
*A21D 8/04* (2006.01)

(52) U.S. Cl.
CPC ............... *C12N 9/20* (2013.01); *A21D 8/042* (2013.01); *C12Y 301/01003* (2013.01)

(58) Field of Classification Search
CPC .............. C12N 9/18; C12N 9/20; A21D 8/04
See application file for complete search history.

(56) References Cited

U.S. PATENT DOCUMENTS

| 6,686,189 B2 | 2/2004 | Rey et al. |
| 8,637,101 B2 | 1/2014 | Laan Van Der et al. |
| 9,187,738 B2 * | 11/2015 | Miasnikov ............. A21D 8/042 |
| 2014/0147552 A1 | 5/2014 | Van Der Laan et al. |

FOREIGN PATENT DOCUMENTS

| WO | 1998026057 A1 | 6/1998 |
| WO | 03/060112 A1 | 7/2003 |
| WO | 2004/099400 A2 | 11/2004 |
| WO | 2005/087918 A2 | 9/2005 |
| WO | 2009/106575 A1 | 9/2009 |
| WO | 2010/134035 A1 | 11/2010 |

OTHER PUBLICATIONS

PCT International Search Report for PCT/EP2017/083526, dated Mar. 7, 2018.
Third party observations for European patent application No. 17829959.0 dated Mar. 1, 2021.
Third party observations for European patent application No. 17829960.8 dated Mar. 1, 2021.

* cited by examiner

*Primary Examiner* — Maryam Monshipouri
(74) *Attorney, Agent, or Firm* — McBee Moore & Vanik IP, LLC

(57) ABSTRACT

The present disclosure describes a variant polypeptide having lipolytic activity, wherein the variant has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, and wherein said variant has at least 70% identity with the mature polypeptide having lipolytic activity as set out in SEQ ID NO: 2. Such a variant polypeptide may be used in the preparation of a baked product.

16 Claims, 2 Drawing Sheets

Specification includes a Sequence Listing.

LIPOLYTIC ENZYME VARIANTS

CROSS-REFERENCE TO RELATED APPLICATIONS

This application is a continuation of U.S. patent application Ser. No. 16/471,121, filed 19 Jun. 2019, which is a National Stage entry of International Application No. PCT/EP2017/083526, filed 19 Dec. 2017, which claims priority to European Patent Application No. 16205906.7, filed 21 Dec. 2016, and European Patent Application No. 17157061.7, filed 21 Feb. 2017. The disclosure of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-511001_ST25.txt" created on 30 Nov. 2020, and 24,548 bytes in size) is submitted concurrently with the instant application, and the entire contents of the Sequence Listing are incorporated herein by reference.

BACKGROUND

Field

The present disclosure relates to a variant polypeptide having lipolytic activity, also referred to as a lipolytic enzyme variant. The disclosure also relates to a nucleic acid sequence encoding such a variant, a nucleic acid construct comprising the nucleic acid sequence and to recombinant host cell comprising a recombinant expression vector comprising said nucleic acid construct encoding the variant. Further, the disclosure relates to a method for producing a lipolytic polypeptide variant. The disclosure further relates to a composition comprising the variant polypeptide, use of such variant polypeptide in the production of a food product and to use of the variant polypeptide to replace at least part of a chemical emulsifier in the production of a dough and/or a baked product. The disclosure further relates to a dough, a process for the production of a dough and a process for the production of a baked product.

Description of Related Art

In the baking industry, e.g. in the industrial dough and bread making, processing aids are used to improve properties of a dough and or a baked product. In order to improve the handling properties of the dough and/or the final properties of the baked products there is a continuous effort to develop processing aids with improved properties. Processing aids are defined herein as compounds that improve the handling properties of the dough and/or the final properties of the baked products. Dough properties that may be improved comprise stability, gas retaining capability, elasticity, extensibility, moldability etcetera. Properties of the baked products that may be improved comprise loaf volume, crust crispiness, oven spring, crumb texture, crumb structure, crumb softness, flavour, relative staleness and shelf life.

These processing aids may be divided into two groups: chemical additives and enzymes (also referred to as baking enzymes).

Chemical additives with improving properties include oxidising agents such as ascorbic acid, bromate and azodicarbonate, reducing agents such as L-cysteine and glutathione, emulsifiers acting as dough conditioners such as diacetyl tartaric acid esters of mono/diglycerides (DATEM), sodium stearoyl lactylate (SSL) or calcium stearoyl lactylate (CSL), emulsifiers acting as crumb softeners such as glycerol monostearate (GMS) etceteras, fatty materials such as triglycerides (fat) or lecithin and others. Emulsifiers such as DATEM, SSL and/or CSL may be used for generating process tolerance. Emulsifiers may also be used to increase volume of a baked product. The resistance of consumers to chemical additives is growing and there is therefore constant need to replace chemical additives such as chemical emulsifiers.

There are currently replacers of chemical emulsifiers in the market such as lipolytic enzymes that upon action of a substrate can generate emulsifying molecules in situ. Lipolytic enzymes are enzymes that catalyse the hydrolysis of ester bonds in lipid substrates, leading to the release of fatty acids. In industry, phospholipases are used to fully or partly replace e.g. DATEM. WO1998026057 describes a phospholipase that can be used in a process for making bread. WO2009/106575 describes a lipolytic enzyme and its use in a process for making bread. Despite the fact that there are commercial lipolytic enzymes in the market there is still an industrial need for lipolytic enzymes with improved performance in industry, especially in the baking industry.

DESCRIPTION OF THE SEQUENCE LISTING

Figure 1:
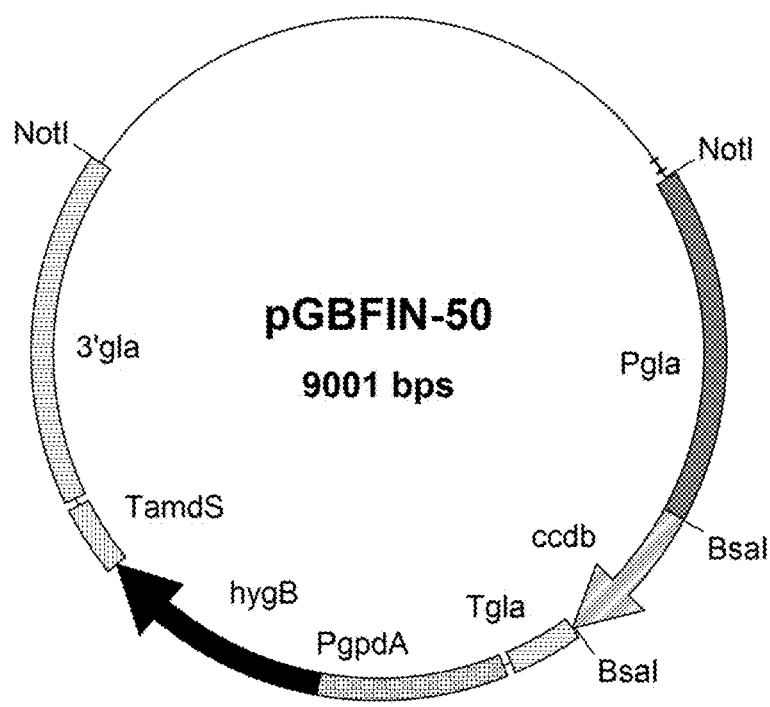
FIG. 1. Sets out the *Aspergillus* expression vector pGBFIN-50.
Figure 2:
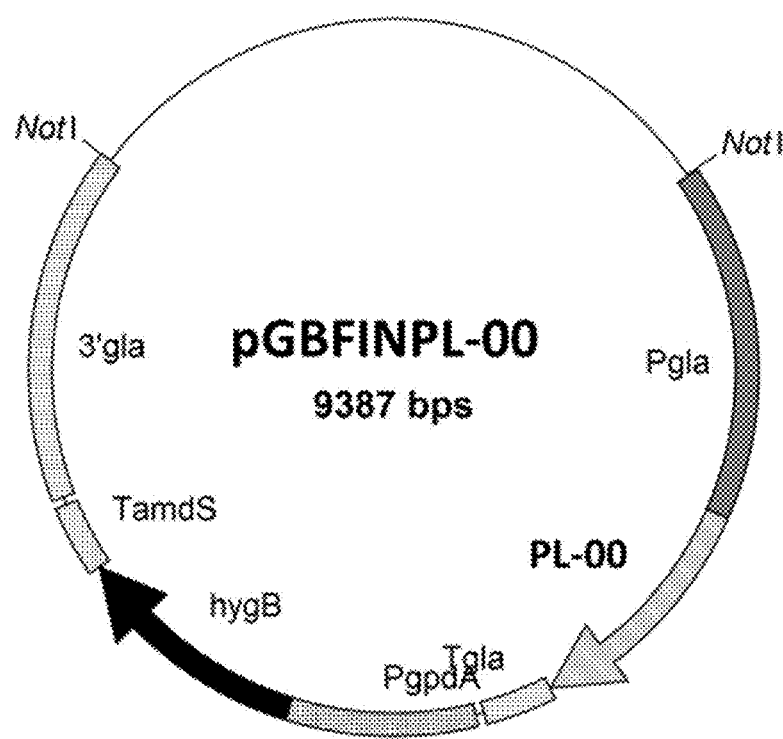
FIG. 2. Sets out the *Aspergillus* lipolytic enzyme expression vector pGBFINPL-00

SEQ ID NO: 1 sets out the polynucleotide sequence encoding the reference polypeptide having lipolytic activity (set out in nucleotides 100 to 914) including an N-terminal signal sequence of 33 amino acids (set out in nucleotides 1 to 99), and C-terminal pro-sequence (set out in nucleotides 915 to 1038).

SEQ ID NO: 2 sets out the amino acid sequence of the reference polypeptide (also referred to as parent polypeptide) having lipolytic activity (set out in amino acids 34 to 304) including an N-terminal signal sequence of 33 amino acids (set out in amino acids 1 to 33), and C-terminal pro-sequence (set out in amino acids 305 to 346)

SEQ ID NO: 3 sets out a modified translational initiation sequence of the glucoamylase glaA promoter.

SEQ ID NO: 4 sets out the amino acid sequence of an *Alicyclobacillus pohliae* alpha-amylase polypeptide.

SEQ ID NO: 5 sets out the amino acid sequence of a *Bacillus stearothermophilus* amylase polypeptide.

SEQ ID NO: 6 sets out the amino acid sequence of an amylase from *Pseudomonas saccharophila*

SEQ ID NO: 7 sets out the amino acid sequence of an amylase.

SUMMARY

According to the disclosure there is provided a variant polypeptide having lipolytic activity, wherein the variant has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, and wherein said variant has at least 70% identity with the mature polypeptide having lipolytic activity as set out in SEQ ID NO: 2.

The disclosure also provides:

a nucleic acid sequence encoding the variant polypeptide of the disclosure;

A nucleic acid construct comprising the nucleic acid sequence operably linked to one or more control sequences capable of directing the expression of a lipolytic enzyme in a suitable expression host.

A recombinant host cell comprising a recombinant expression vector comprising the nucleic acid construct.

The disclosure also relates a method for producing a lipolytic polypeptide variant comprising cultivating the host cell under conditions conducive to production of the lipolytic enzyme variant and recovering the lipolytic enzyme variant.

Further the disclosure relates to:

A composition comprising the variant polypeptide of the disclosure;

Use of the variant polypeptide according to the disclosure, or of the composition according to the disclosure in the production of a food product, preferably in the production of a dough and/or a baked product A dough comprising the variant polypeptide according to the disclosure, a variant polypeptide obtainable by the method according to the disclosure or the composition according to the disclosure.

A process for the production of a dough comprising the step of combining an effective amount of the variant polypeptide according to the disclosure, the variant polypeptide obtainable by the method according to the disclosure or the composition according to the disclosure to at least one dough ingredient.

A process for the production of a baked product, which method comprises baking the dough according to the disclosure.

DETAILED DESCRIPTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The present disclosure concerns variant polypeptides having lipolytic activity. The variant polypeptides according to the disclosure have at least one altered property as compared with a reference polypeptide having lipolytic activity. In an aspect of the variant polypeptide, the reference polypeptide comprises the mature lipolytic enzyme as set out in SEQ ID NO: 2. In a further aspect of the variant polypeptide, the reference polypeptide is the mature lipolytic enzyme as set out in SEQ ID NO: 2.

The variant has at least 70% identity with the mature polypeptide having lipolytic activity as set out in SEQ ID NO: 2. In an aspect of the variant polypeptide, the mature polypeptide comprises an amino acid sequence as set out in amino acids 34 to 304 of SEQ ID NO: 2. In a further aspect of the variant polypeptide, the mature polypeptide has an amino acid sequence as set out in amino acids 34 to 304 of SEQ ID NO: 2.

The reference polypeptide may also be referred to herein as a parent polypeptide or comparison polypeptide.

A variant polypeptide according to the disclosure may be an isolated, substantially pure, pure, recombinant or synthetic polypeptide.

In an embodiment, the variant polypeptide according to the disclosure is a non-naturally occurring polypeptide.

Herein, positions which may be substituted to achieve a variant of the disclosure are defined with reference to SEQ ID NO: 2. The variant has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2.

More concretely, the disclosure relates to a variant polypeptide having lipolytic activity, wherein the variant has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, and wherein said variant has at least 70% identity with the mature polypeptide having lipolytic activity as set out in SEQ ID NO: 2.

In an embodiment the mature polypeptide comprises an amino acid sequence as set out in amino acids 34 to 304 of SEQ ID NO: 2. In an embodiment the reference polypeptide having lipolytic activity comprises an amino acid sequence as set out in amino acids 34 to 304 of SEQ ID NO: 2. In an embodiment of the variant polypeptide according to the disclosure, the reference polypeptide comprises an amino acid sequence as set out in amino acids 34 to 304 of SEQ ID NO: 2 and the mature polypeptide comprises an amino acid sequence as set out in amino acids 34 to 304 of SEQ ID NO: 2.

In a further embodiment, such variant has one or more altered properties as compared to the reference polypeptide having lipolytic activity as set out in amino acids 34 to 304 of SEQ ID NO: 2 measured under the same conditions, and said variant has at least 70% identity with the mature polypeptide having lipolytic activity as set out in amino acids 34 to 304 of SEQ ID NO: 2.

In an embodiment, the variant polypeptide according to the disclosure has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, and wherein the variant has one or more altered properties as compared with a reference polypeptide having lipolytic activity and wherein said variant has at least 70% identity with the mature polypeptide having lipolytic activity as set out in SEQ ID NO: 2.

In an embodiment, the variant polypeptide according to the disclosure has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, and wherein the variant has an altered ratio of the activity on polar lipids:activity on non-polar lipids as compared with a reference polypeptide having lipolytic activity and wherein said variant has at least 70% identity with the mature polypeptide having lipolytic activity as set out in SEQ ID NO: 2.

In an embodiment, the variant polypeptide according to the disclosure has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, wherein the variant has an increased ratio of the activity on polar lipids:activity on non-polar lipids as compared to the reference polypeptide having lipolytic activity measured under the same conditions, and wherein said variant has at least 70% identity with the mature polypeptide having lipolytic activity as set out in SEQ ID NO: 2.

In an embodiment the mature polypeptide comprises an amino acid sequence as set out in amino acids 34 to 304 of SEQ ID NO: 2. In an embodiment the reference polypeptide having lipolytic activity comprises an amino acid sequence as set out in amino acids 34 to 304 of SEQ ID NO: 2. In an embodiment of the variant polypeptide according to the disclosure, the reference polypeptide comprises an amino acid sequence as set out in amino acids 34 to 304 of SEQ ID NO: 2 and the mature polypeptide comprises an amino acid sequence as set out in amino acids 34 to 304 of SEQ ID NO: 2.

In a further embodiment, such variant has one or more altered properties as compared to the reference polypeptide having lipolytic activity as set out in amino acids 34 to 304 of SEQ ID NO: 2 measured under the same conditions, and said variant has at least 70% identity with the mature polypeptide having lipolytic activity as set out in amino acids 34 to 304 of SEQ ID NO: 2.

In an embodiment, the variant polypeptide according to the disclosure has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, the variant has an increased ratio of the activity on polar lipids:activity on non-polar lipids as compared to the reference polypeptide having lipolytic activity as set out in amino acids 34 to 304 of SEQ ID NO: 2 measured under the same conditions, and said variant has at least 70% identity with the mature polypeptide having lipolytic activity as set out in amino acids 34 to 304 of SEQ ID NO: 2.

In an aspect the lipolytic enzyme variant according to the disclosure, is a lipolytic enzyme variant having at least 70% identity, in an aspect at least 75% identity, in an aspect at least 80% identity, in an aspect at least 85% identity, in an aspect at least 90% identity, in an aspect at least 95% identity, in an aspect at least 96% identity, in an aspect at least 97% identity, in an aspect at least 98% identity, in an aspect at least 99% identity, with the mature polypeptide having lipolytic activity as set out in the amino acids sequence of SEQ ID NO: 2.

In an aspect the lipolytic enzyme variant according to the disclosure, is a lipolytic enzyme variant having at least 70% identity, in an aspect at least 75% identity, in an aspect at least 80% identity, in an aspect at least 85% identity, in an aspect at least 90% identity, in an aspect at least 95% identity, in an aspect at least 96% identity, in an aspect at least 97% identity, in an aspect at least 98% identity, in an aspect at least 99% identity, with the mature polypeptide having lipolytic activity as set out in amino acids 34 to 304 of SEQ ID NO: 2.

The lipolytic enzyme variant of the disclosure may comprise one or more a substitutions at the positions disclosed herein. The lipolytic enzyme variant of the disclosure may for example comprise two, at least two, at least three, at least four, at least 5, at least 10, at least 15 or at least 20 of the disclosed positions.

The lipolytic enzyme variant of the disclosure may comprise one or more further substitutions not disclosed herein as long as the variant has one or more altered properties, as described herein, as compared with a reference polypeptide having lipolytic activity. The one or more further substitutions may be selected from any of the positions 53, 112, 113, 117, 122, 124, 138, 141, 178, 179, 182, 200, 202, 203, 229, 238, 282, 284, 286, 295, said positions being defined with reference to SEQ ID NO: 2. Preferred further substitutions are listed below and in Table 1 (with the positions being defined in relation to the sequence set out in SEQ ID NO: 2). A variant of the disclosure may be generated using any combination of substitutions listed in claim 1 and below or in Table 1.

A "substitution" in this context indicates that a position in the variant which corresponds to one of the positions set out above in SEQ ID NO: 2 comprises an amino acid residue which does not appear at that position in the reference polypeptide having lipolytic activity Amino acids changes are depicted according to the single letter annotation.

The disclosure provides a variant polypeptide according to the disclosure, wherein the reference polypeptide comprises an amino acid sequence as set out in amino acids 34 to 304 of SEQ ID NO: 2 and wherein the mature polypeptide comprises an amino acid sequence as set out in amino acids 34 to 304 of SEQ ID NO: 2.

In an embodiment the mature polypeptide has an amino acid sequence as set out in amino acids 34 to 304 of SEQ ID NO: 2. In an embodiment the reference polypeptide having lipolytic activity has an amino acid sequence as set out in amino acids 34 to 304 of SEQ ID NO: 2.

Mature Polypeptide

The lipolytic enzyme variant as the disclosure is a mature polypeptide.

A "mature polypeptide" is defined herein as a polypeptide in its final form and is obtained after translation of an mRNA into polypeptide and post-translational modifications of said polypeptide. Post-translational modification include N-terminal processing, C-terminal truncation, glycosylation, phosphorylation and removal of leader sequences such as signal peptides, propeptides and/or prepropeptides by cleavage. The process of maturation may depend on the particular expression vector used, the expression host and the production process. Preferably, the mature polypeptide having lipolytic activity in the amino acid sequence as set out in SEQ ID NO: 2 is the polypeptide as set out in amino acids 34 to 304 of SEQ ID NO: 2.

A "mature polypeptide coding sequence" means a polynucleotide that encodes a mature polypeptide (with reference to its amino acid sequence).

A "nucleotide sequence encoding a mature polypeptide" is defined herein as the polynucleotide sequence which codes for a mature polypeptide.

As is known to the person skilled in the art it is possible that the N-terminus of a mature polypeptide might be heterogeneous due to processing errors during secretion and/or maturation. As is known to the person skilled in the art it is possible that the C-terminus of a mature polypeptide, might be heterogeneous due to processing errors during secretion and/or maturation. In particular such processing errors might occur upon overexpression of the polypeptide. In addition, exo-protease activity might give rise to heterogeneity. The extent to which heterogeneity occurs depends also on the host and fermentation protocols that are used. Such C-terminal processing artefacts might lead to a shorter or a longer mature polypeptide. Processing errors during secretion and/or maturation may also lead to a heterogeneous N-terminus.

In an embodiment the lipolytic enzyme variant contains one or more additional residues and starts at position −1, or −2, or −3 etc. said position being defined with reference to position 34 of SEQ ID NO: 2. In such event the N terminus starts at position 33, or 32, or 31 etc.

Alternatively, it might lack certain residues and as a consequence starts at position 2, or 3, or 4 etc. said position being defined with reference to position 34 of SEQ ID NO: 2. In such event the N terminus starts at position 35, or 36, or 37 etc.

Further, also additional residues may be present at the C-terminus, e.g. the C-terminus ends at position 305, 306 etc. Alternatively, the C-terminus might lack certain residues and as a consequence end at position 303, or 302 etc.

In an aspect, the mature enzyme comprises the polypeptide as set out in amino acids 34 to 303 of SEQ ID NO: 2.

In an aspect, the mature enzyme comprises the polypeptide as set out in amino acids 31 to 304 of SEQ ID NO: 2.

In an aspect, the mature enzyme comprises the polypeptide as set out in amino acids 31 to 303 of SEQ ID NO: 2.

In an aspect, the mature enzyme comprises the polypeptide as set out in amino acids 34 to 307 of SEQ ID NO: 2.

In an aspect, the mature enzyme comprises the polypeptide as set out in amino acids 34 to 302 of SEQ ID NO: 2. In an aspect, the mature enzyme comprises the polypeptide as set out in amino acids 31 to 307 of SEQ ID NO: 2.

In an embodiment, the variant polypeptide according to the disclosure, the variant has an amino acid sequence which, when aligned with the amino acid sequence as set out in SEQ ID NO: 2, comprises one or more of the amino acid substitutions selected from

I113H
I113L
I113N
I113R
I113T
L122A
L122M
H138E
H138S
F141M
F141Y

-continued

V179L
V179M
V179S
L282E
L282F
L282K
L282M
L282N
L282R
L282S
L282T
I284A
I284D
I284E
I284M
I284N
I284P
I284Q
I284S
I284T
A286L
D295E
D295G
D295N
D295S said positions being defined with reference to SEQ ID NO: 2, and wherein said variant has at least 70% identity with the mature polypeptide having lipolytic activity as set out in SEQ ID NO: 2. In a further embodiment such variant has one or more altered properties as compared with a reference polypeptide having lipolytic activity. In a further embodiment such variant has one or more altered properties as compared to the reference polypeptide having lipolytic activity as set out in amino acids 34 to 304 of SEQ ID NO: 2 measured under the same conditions, and said variant has at least 70% identity with the mature polypeptide having lipolytic activity as set out in amino acids 34 to 304 of SEQ ID NO: 2.

In an embodiment the variant polypeptide according to the disclosure has an amino acid sequence which, when aligned with the amino acid sequence as set out in SEQ ID NO: 2, comprises one or more of the amino acid substitutions selected from the substitutions listed above, has an altered ratio of the activity on polar lipids:activity on non-polar lipids as compared with a reference polypeptide having lipolytic activity and wherein said variant has at least 70% identity with the mature polypeptide having lipolytic activity as set out in SEQ ID NO: 2.

In an embodiment, the variant polypeptide according to the disclosure has an amino acid sequence which, when aligned with the amino acid sequence as set out in SEQ ID NO: 2, comprises one or more of the amino acid substitutions selected from I113H
I113L
I113N
I113R
I113T
L122A
L122M
H138E
H138S
F141M
F141Y
V179L
V179M
V179S
L282E -continued L282F
L282K
L282M
L282N
L282R
L282S
L282T
I284A
I284D
I284E
I284M
I284N
I284P
I284Q
I284S
I284T
A286L
D295E
D295G
D295N
D295S said positions being defined with reference to SEQ ID NO: 2, and wherein said variant has at least 70% identity with the mature polypeptide having lipolytic activity as set out in SEQ ID NO: 2. In a further embodiment the variant has one or more altered properties (preferably has an increased ratio of the activity on polar lipids:activity on non-polar lipids) as compared with a reference polypeptide having lipolytic activity. In a further embodiment such variant has an increased ratio of the activity on polar lipids:activity on non-polar lipids as compared to the reference polypeptide having lipolytic activity as set out in amino acids 34 to 304 of SEQ ID NO: 2 measured under the same conditions, and said variant has at least 70% identity with the mature polypeptide having lipolytic activity as set out in amino acids 34 to 304 of SEQ ID NO: 2.

In an embodiment the variant polypeptide according to the disclosure has an amino acid sequence which, when aligned with the amino acid sequence as set out in SEQ ID NO: 2, comprises one or more of the amino acid substitutions selected from the substitutions listed above, has an altered ratio of the activity on polar lipids:activity on non-polar lipids as compared with a reference polypeptide having lipolytic activity and wherein said variant has at least 70% identity with the mature polypeptide having lipolytic activity as set out in SEQ ID NO: 2.

Variant Polypeptide Having Lipolytic Activity

A lipolytic enzyme demonstrates lipolytic activity, i.e. it is able to catalyse the hydrolysis of ester bonds in lipids, such as triglycerides and/or galactolipids and/or phospholipids. In particular lipolytic enzyme variants according to the disclosure demonstrate lipolytic activity on lipids present in flour. Flour includes cereal flour, corn flour, rice flour. Flour herein includes whole-meal flour.

Wheat flour contains approximately 2-3% lipids. The flour lipids can be divided into starch lipids (0.8-1%) and non-starch lipids (1.4-2.0%). Whereas the starch lipids consist mainly of polar lysophospholipids, the non-starch lipids consist of about 40% neutral triglycerides and 40% polar phospho- and glycolipids. For optimisation of the flour lipids fraction the lipolytic polypeptide variant according to the disclosure is in an aspect capable of hydrolysis of the polar lipids, being the phospholipids and glycolipids (more specifically the galactolipids) in situ in the dough by adding the lipolytic enzyme variant according to the disclosure.

The lipolytic activity of the lipolytic enzyme variants according to the disclosure may be determined by any suitable method, e.g. by assays known in the art or described later herein. A variant polypeptide having lipolytic activity and lipolytic polypeptide variant, a lipolytic enzyme variant and a variant polypeptide are used interchangeably herein. A polypeptide having lipolytic activity, a lipolytic polypeptide, and a lipolytic enzyme are used interchangeably herein. The variants described herein are collectively comprised in the terms "a lipolytic polypeptide variant according to the disclosure" or "a lipolytic enzyme variant according to the disclosure" or "a variant polypeptide according to the disclosure".

A triacylglycerol lipase (EC 3.1.1.3) demonstrates catalytic hydrolytic activity on one or more ester bonds in triglycerides (also known as triacylglycerol or triacylglycerides). The wordings "activity on triacylglycerols (TAG)" and "TAG-lipase activity" are used interchangeably herein. The wordings "triglycerides" and "triacylglycerides" and "triacylglycerols" are used interchangeably herein In general triglycerides and triglyceride are used interchangeably herein: they both refer to the compound class.

A galactolipase demonstrates galactolipase activity (EC 3.1.1.26). Galactolipase activity is catalytic hydrolytic activity on one or more bonds in the galactolipids. The wordings "galactolipase activity" and "activity on galactolipids" are used interchangeably herein.

Galactolipids consist of a glycerol backbone with esterified fatty acid, while the third hydroxyl group is bound to sugar residues such as in case of galactolipids a galactose, for example monogalactosyldiglyceride or digalactosyldiglyceride. In general, galactolipids and galactolipid are used interchangeably herein: they both refer to the compound class. In wheat, galactolipids are mainly present as diacylgalactolipids. In an aspect of the disclosure the galactolipids are DGDG (digalactosyldiglycerides) or MGDG (monogalactosyldiglycerides).

A phospholipase demonstrates phospholipase activity. Phospholipase activity is a catalytic hydrolytic activity on one or more bonds in the phospholipids. The wordings "phospholipase activity" and "activity on phospholipids" are used interchangeably herein. Phospholipids consist of a glycerol backbone with esterified fatty acid, while the third hydroxyl group of the glycerol is esterified with phosphoric acid. The phosphoric acid may, in turn, be esterified to for example an amino alcohol like ethanolamine (phosphatidylethanolamine), choline (phosphatidylcholine). Several types of phospholipase activity can be distinguished which hydrolyse the ester bond(s) that link the fatty acyl moieties to the glycerol backbone:

Phospholipase A1 and A2 activity concern the deacylation of one fatty acyl group in the outer sn-1 and middle sn-2 positions respectively, from a diacylglycerophospholipid to produce a lysophospholipid. This is a desirable activity for emulsifier replacement. Phospholipase A1 has EC number EC 3.1.1.32 and phospholipase A2 EC 3.1.1.4.

Lysophospholipase activity (also called phospholipase B activity) concerns the hydrolysis of the remaining fatty acyl group in a lysophospholipid. For emulsifier replacement lysophospholipase activity is usually less desirable. Lysophospholipase has EC number EC 3.1.1.5.

In general phospholipids and phospholipid are used interchangeably herein: they both refer to the compound class. In an aspect of the disclosure phospholipids are phosphatidylcholines (PC).

Lipolytic enzymes are usually classified according to the bonds that they preferentially cleave, but can show some activity beyond their most preferred substrates. For example, a PLA1 phospholipase may show greatest activity towards the cleavage of acyl chains from the sn1 position of the glycerol backbone of a phospholipid, but some activity on TAG, galactolipids and sn2 hydrolysis may also occur.

The wordings "ratio of the activity on galactolipids:the activity on triacylglycerols" and "galactolipase:TAG-lipase activity ratio" and "galactolipase to TAG-lipase activity ratio" and "ratio of the galactolipase activity:the TAG-lipase activity" are used interchangeably herein.

The wordings "ratio of the activity on phospholipids:the activity on triacylglycerols" and "phospholipase:TAG-lipase activity ratio" and "phospholipase to TAG-lipase activity ratio" and "ratio of the phospholipase activity:the TAG-lipase activity" are used interchangeably herein.

Polar lipids herein include phospholipids and galactolipids.

Non-polar lipids herein include triglycerides and/or diglycerides. The non-polar lipid can be triolein.

Herein esters of long chain fatty acids are esters of C12-C18 fatty acids, for instance esters of C16-C18 fatty acids, for instance esters of 018 fatty acids, for instance esters of 018:2 fatty acids.

Herein esters of short chain fatty acids are esters of C4-C8 fatty acids, for instance esters of C4-C6 fatty acids, for instance esters of C4 fatty acids.

The ester of the short chain fatty can be pNP-butyrate.

The ester of the long chain fatty can be pNP-lineolate, pNP-oleate, pNP-stearate or pNP-palmitate.

The ester of the non-saturated chain fatty can be pNP-lineolate or pNP-oleate.

The ester of the saturated chain fatty can be pNP-stearate or pNP-palmitate.

Altered/Improved Property

A variant polypeptide according to the disclosure will typically have an altered property as compared to a reference polypeptide. In particular, the variant polypeptide will have an improved property as compared to a reference polypeptide which is relevant to the use of the variant polypeptide in the food industry, preferably in the preparation of a dough and/or a baked product.

The altered, typically improved, property may be demonstrated by making a dough and/or baked product comprising the lipolytic enzyme variant of the disclosure and another comprising a reference polypeptide having lipolytic activity under the same conditions and comparing the results. The improved property may be demonstrated with the methods and assays described herein. Organoleptic qualities may be evaluated using procedures well established in the baking industry, and may include, for example, the use of a panel of trained taste-testers.

The altered, typically improved, property may be demonstrated in an assay or (bio)chemical analysis.

A variant polypeptide which exhibits a property which is improved in relation to the reference polypeptide having lipolytic activity is one which demonstrates a measurable reduction or increase in the relevant property, typically such that the variant is more suited to use as set out herein, for example in a process for the production of a baked product.

The property may thus be decreased by at least 10%, at least 20%, at least 30%, at least 40% at least 50%, at least 60%, at least 70%, at least 80%, at least 90%, at least 95% or at least 99%. Alternatively, the property may be increased by at least 10%, at least 25%, at least 50%, at least 100%, at least, 200%, at least 500% or at least 1000%. The percentage decrease or increase in this context represents the percentage decrease or increase in comparison to the reference polypeptide having lipolytic activity. It is well known to the skilled person how such percentage changes may be measured—it is a comparison of the property of the reference polypeptide having lipolytic activity and the lipolytic enzyme variant under the same conditions.

The lipolytic enzyme variant according to the disclosure, the composition according to the disclosure and/or the pre-mix according to the disclosure typically result in an improved property in the production of a food product or in an improved property of the food product itself. In particular an improved property of a dough comprising the variant polypeptide according to the disclosure and/or an improved property of a baked product made using the variant polypeptide according to the disclosure.

The term "improved property" herein includes any property of a dough and/or a product obtained from the dough, particularly a baked product, which is improved by the action of the lipolytic enzyme variant, the composition according to the disclosure or the pre-mix according to the disclosure relative to a dough or baked product in which a reference polypeptide is incorporated.

The improved property may include one or more of, but is not limited to, an increased strength of the dough; an increased elasticity of the dough; increased stability of the dough; an improved extensibility of the dough; an increased volume of the baked product; improved flavour of the baked product; improved crumb structure of the baked product improved crispiness; improved oven spring; reduced hardness of a baked product, such as reduced hardness after storage.

The improved property may include a reduced of hardness after storage of a baked product.

The improved property may be determined by comparison of a dough and/or a baked product prepared with and without addition of the (isolated) polypeptide of the present disclosure in accordance with the methods of present disclosure which are described below in the Examples. Organoleptic qualities may be evaluated using procedures well established in the baking industry, and may include, for example, the use of a panel of trained testers, e.g. taste-testers, texture-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to forming faults as a consequence of mechanical abuse, and thus better at maintaining its shape and volume and is evaluated by the ratio of height:width of a cross section of a loaf after normal and/or extended proof.

The term "improved extensibility of the dough" is defined herein as the property of a dough that can be subjected to increased strain or stretching without rupture.

An improved dough stability may be an improved shock resistance of a dough. Improved shock resistance of a dough may be demonstrated as follows.

Bread tins filled with well proofed dough (void volume of >70%) undergo controlled jarring or shocking for example by dropping a tin from set height, e.g. 9 cm height, just before they enter the oven to be baked. This may be done by simultaneously pulling away 2 blocks having this drop-height from below the bottom of the tin. This way the tin drops over the drop-height and the dough experiences a shock. The shock resistance of a dough is improved if, after baking the dough, the volume of the loaf is larger as compared to a reference loaf (which may also be called a control loaf) and/or if the hardness of the loaf after baking the dough is lower as compared to a reference loaf (which may also be called a control).

The term "increased volume of the baked product" is preferably measured as the volume of a given loaf of bread determined by an automated bread volume analyser (e.g. BVM-3, TexVol Instruments AB, Viken, Sweden), using ultrasound or laser detection as known in the art. In case the volume is increased, the property is improved. Alternatively, the height of the baked product after baking in the same size tin is an indication of the baked product volume. In case the height of the baked product has increased, the volume of the baked product has increased.

The term "improved flavor of the baked product" is evaluated by a trained test panel.

The term "improved crumb structure of the baked product" herein includes the property of a baked product with finer cells and/or thinner cell walls in the crumb and/or more uniform/homogenous distribution of gas cells in the crumb and is usually evaluated visually by the baker or by digital image analysis as known in the art (e.g. C-cell, Calibre Control International Ltd, Appleton, Warrington, UK).

The term "improved crispiness" is defined herein as the property of a baked product to give a crispier sensation than a reference product as known in the art, as well as to maintain this crispier perception for a longer time than a reference product. This property can be quantified by measuring a force versus distance curve at a fixed speed in a compression experiment using e.g. a texture analyzer TA-XT Plus (Stable Micro Systems Ltd, Surrey, UK), and obtaining physical parameters from this compression curve, viz. (i) force of the first peak, (ii) distance of the first peak, (iii) the initial slope, (iv) the force of the highest peak, (v) the area under the graph and (vi) the amount of fracture events (force drops larger than a certain preset value). Indications of improved crispness are a higher force of the first peak, a shorter distance of the first peak, a higher initial slope, a higher force of the highest peak, higher area under the graph and a larger number of fracture events. A crispier product should score statistically significantly better on at least two of these parameters as compared to a reference product. In the art, "crispiness" is also referred to as crispness, crunchiness or crustiness, meaning a material with a crispy, crunchy or crusty fracture behaviour.

Oven spring is in bread making defined as the final burst of rising of a loaf, such as a baguette, a batard or a boule, after it is transferred to the oven and before the crust hardens. In some types of bread oven spring is a desired property and is induced in a defined manner by slashing the dough before it is baked. Slashing is a term that refers to the process of cutting through the dough skin with a sharp knife. Baguettes are typically made with 3 or 5 diagonal slashes. Oven spring may be assessed visually, for example by an experienced baker judging or ranking the oven spring. E.g. Oven spring: 1=incision closed completely to 5=completely open incision; teared. The oven spring of the baked product may be determined by measuring the crust opening at the largest width of the crust opening after baking the dough and cooling the baked product to ambient temperature. An increased oven spring is usually considered an improved oven spring. For some baked products, an oven spring having a more rough, jaggered or hairy edge is desirable and considered an improved oven spring.

The term "hardness of the baked product" is the opposite of "softness" and is defined herein as the property of a baked product that is less easily compressed. Hardness (which may also be referred to as "firmness") may be evaluated either empirically by a skilled baker or measured by the use of a texture analyzer (e.g. TAXT Plus) as known in the art. The hardness measured within 24 hours after baking is called initial hardness. The hardness measured 24 hours or more after baking is called hardness after storage, for example after storage for 1, 2, 3, 4 or 6 weeks. A reduced hardness may be demonstrated as a reduced initial hardness and/or as a reduced hardness after storage. A reduced hardness may be demonstrated by a reduced increase of hardness after storage.

The lipolytic enzyme variant according to the disclosure, the composition according to the disclosure and/or the pre-mix according to the disclosure may result in an improved process for the production a dough (e.g. an increased strength of the dough; an increased stability of the dough and/or an improved extensibility of the dough) and/or an improved process for the production of a baked product (e.g. an increased strength of the dough; an increased stability of the dough and/or an improved extensibility of the dough) and/or a baked product having at least one improved property.

Typically, the altered properties are determined at ambient conditions. Ambient conditions as used herein include a temperature of 20 to 25 degrees C. and a moisture level of 40% humidity. Ambient conditions herein include a temperature of 20 degrees C. and a moisture level of 40% humidity.

The lipolytic enzyme variant according to the disclosure has one or more altered properties as compared with a reference polypeptide having lipolytic activity and wherein said variant has at least 70% identity with the mature polypeptide having lipolytic activity as set out in SEQ ID NO: 2.

As indicated above the altered, typically improved, property may be demonstrated in an assay or (bio)chemical analysis. An assay performed at pH 7 or 8 is thought to be more suitable to obtain information concerning the preparation of baked products of more alkaline nature, such as cake. An assay performed at pH 5.5 is thought to be more suitable to obtain information concerning the preparation of baked products of more acidic nature, such as bread.

The altered property may include an increased ratio of the activity on polar lipids:activity on non-polar lipids as compared to the reference polypeptide having lipolytic activity measured under the same conditions.

Ratio of the Activity on Polar Lipids:Activity Non-Polar Lipids

In an embodiment of the variant polypeptide according to the disclosure the altered property includes an increased ratio of the activity on polar lipids:activity on non-polar lipids as compared to the reference polypeptide having lipolytic activity measured under the same conditions.

The disclosure provides lipolytic enzyme variants having an increased ratio of the activity on polar lipids:activity on non-polar lipids as compared to the reference polypeptide having lipolytic activity measured under the same conditions.

In an embodiment the variant polypeptide according to the disclosure has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295, said positions being defined with reference to SEQ ID NO: 2, and wherein the variant has an increased ratio of the activity on polar lipids:activity on non-polar lipids as compared to a reference polypeptide having lipolytic activity measured under the same conditions and wherein said variant has at least 70% identity with an amino acid sequence as set out in amino acids 34 to 304 of SEQ ID NO: 2

In an embodiment of the variant polypeptide according to the disclosure, the reference polypeptide comprises an amino acid sequence as set out in amino acids 34 to 304 of SEQ ID NO: 2 and the mature polypeptide comprises an amino acid sequence as set out in amino acids 34 to 304 of SEQ ID NO: 2.

In an embodiment the variant polypeptide according to the disclosure, the variant has an amino acid sequence which, when aligned with the amino acid sequence as set out in SEQ ID NO: 2, comprises one or more of the amino acid substitutions selected from

| |
|---|
| I113H |
| I113L |
| I113N |
| I113R |
| I113T |
| L122A |
| L122M |
| H138E |
| H138S |
| F141M |
| F141Y |
| V179L |
| V179M |
| V179S |
| L282E |
| L282F |
| L282K |
| L282M |
| L282N |
| L282R |
| L282S |
| L282T |
| I284A |
| I284D |
| I284E |
| I284M |
| I284N |
| I284P |
| I284Q |
| I284S |
| I284T |
| A286L |
| D295E |
| D295G |
| D295N |
| D295S | said position being defined with reference to SEQ ID NO: 2 and wherein the variant has an increased ratio of the activity on polar lipids:activity on non-polar lipids as compared to a reference polypeptide having lipolytic activity measured under the same conditions and wherein said variant has at least 70% identity with an amino acid sequence as set out in amino acids 34 to 304 of SEQ ID NO: 2.

The determination of the activity on polar lipids may be done via measuring using suitable assays at pH 5.5 such as Assay 2A, using DGDG as substrate.

The determination of the activity on polar lipids may be done via measuring using suitable assays at pH 7 such as analogous to Assay 2A, using DGDG as substrate and using a pH 7 buffer.

The determination of the activity on polar lipids may be done via measuring using suitable assays at pH 8 such as Assay 2B, using DGDG as substrate.

The determination of the activity on polar lipids may be done via measuring using suitable assays at pH 5.5 such as analogous Assay 2A, using MGDG as substrate.

The determination of the activity on polar lipids may be done via measuring using suitable assays at pH 7 such as analogous to Assay 2A, using MGDG as substrate and using a pH 7 buffer.

The determination of the activity on polar lipids may be done via measuring using suitable assays at pH 8 such as analogous to Assay 2B, using MGDG as substrate.

The determination of the activity on polar lipids may be done via measuring using suitable assays at pH 5.5 such as Assay 1A, using PC as substrate.

The determination of the activity on polar lipids may be done via measuring using suitable assays at pH 7 such as analogous to Assay 1A, using PC as substrate and using a pH 7 buffer.

The determination of the activity on polar lipids may be done via measuring using suitable assays at pH 8 such as Assay 1B, using PC as substrate.

The determination of the activity on non-polar lipids may be done via measuring using suitable assays at pH 5.5 such as Assay 3A, using Triolein as substrate.

The determination of the activity on non-polar lipids may be done via measuring using suitable assays at pH 7 such as analogous to Assay 3A, using Triolein as substrate and using a pH 7 buffer.

The determination of the activity on non-polar lipids may be done via measuring using suitable assays at pH 8 such as to Assay 3B, using Triolein as substrate.

The ratio of the activity on polar lipids:activity non-polar lipids may be determined via measuring the particular activities using suitable assays as described herein and calculating the ratio analogous to "Exemplary determination and calculation of galactolipase to TAG-lipase activity ratio of variant #" in the Materials and Methods herein.

For example the ratio of the activity on polar lipids: activity non-polar lipids at pH 5.5 may be determined by applying suitable assays at pH 5.5 as described herein (e.g. applying Assay 2A, Assay 3A) and calculating the ratio according to "Exemplary determination and calculation of galactolipase to TAG-lipase activity ratio of variant #" in the Materials and Methods herein.

Alternatively the ratio of the activity on polar lipids: activity non-polar lipids at pH 5.5 may be determined by applying suitable assays at pH 5.5 as described herein (e.g. applying Assay 1A, Assay 3A) and calculating the ratio analogous to "Exemplary determination and calculation of galactolipase to TAG-lipase activity ratio of variant #" in the Materials and Methods herein.

More examples to determine the ratio of the activity on polar lipids:activity on non-polar lipids are given in the Example section herein. See "Determination of altered properties" and Tables 2 to 5 thereafter.

Galactolipids, Ratio of the Activity on Galactolipids:the Activity on Triglycerides.

In an aspect of the disclosure the increased ratio of the activity on polar lipids:the activity on non-polar lipids as compared to the reference polypeptide having lipolytic activity measured under the same conditions is an increased ratio of the activity on galactolipids:the activity on triglycerides as compared to the reference polypeptide having lipolytic activity (such as the polypeptide of SEQ ID NO: 2) measured under the same conditions.

The ratio of the activity on galactolipids:the activity on triglycerides is determined at a certain pH, such as pH 5.5 or pH7 or pH 8.

In an aspect of the disclosure the increased ratio of the activity on galactolipids:the activity on triglycerides is determined at pH 5.5.

In an aspect of the disclosure the increased ratio of the activity on galactolipids:the activity on triglycerides is determined at pH 8.

The determination of the ratio of the activity on galactolipids:the activity on triglycerides may be done via measuring using suitable assays at as described above e.g. for pH 5.5, by Measuring activity on polar lipids using DGDG as substrate (Assay 2A);
Measuring activity on non-polar lipids using Triolein as substrate (Assay 3A);
and calculating the ratio (see "Exemplary determination and calculation of galactolipase to TAG-lipase activity ratio of variant #" in the Materials and Methods herein).

The determination of the ratio of the activity on galactolipids:the activity on triglycerides may be done via measuring using suitable assays at pH 8 such as Assays 2B and 3B as described herein and calculating the ratio (see "Exemplary determination and calculation of galactolipase to TAG-lipase activity ratio of variant #" in the Materials and Methods herein).

In an aspect of the disclosure the increased ratio of the activity on galactolipids:the activity on triglycerides is an increased ratio of the activity on DGDG activity:the activity on Triolein.

In an aspect of the disclosure the ratio of the activity on DGDG activity:the activity on Triolein is determined at pH 5.5. (E.g. Assays 2A and 3A and calculating the ratio as described herein)

In an aspect of the disclosure the ratio of the activity on DGDG activity:the activity on Triolein is determined at pH 8. (E.g. Assays 2B and 3B and calculating the ratio as described herein)

Phospholipids, Ratio of the Activity on Phospholipids:the Activity on Triglycerides In an aspect of the disclosure the increased ratio of the activity on polar lipids:the activity on non-polar lipids as compared to the reference polypeptide having lipolytic activity (such as the polypeptide of SEQ ID NO: 2) measured under the same conditions is an increased ratio of the activity on phospholipids:the activity on triglycerides as compared to the reference polypeptide having lipolytic activity (such as the polypeptide of SEQ ID NO: 2) measured under the same conditions.

The ratio of the activity on phospholipids:the activity on triglycerides is determined at a certain pH, such as pH 5.5 or pH7 or pH 8.

In an aspect of the disclosure the increased ratio of the activity on phospholipids:the activity on triglycerides is determined at pH 5.5.

In an aspect of the disclosure the increased ratio of the activity on phospholipids:the activity on triglycerides is determined at pH 8.

The determination of the ratio of the activity on phospholipids:the activity on triglycerides may be done via measuring using suitable assays at as described above e.g. for pH 5.5, by Measuring activity on polar lipids using PC as substrate (Assay 1A);
Measuring activity on non-polar lipids using Triolein as substrate (Assay 3A);
and calculating the ratio analogous to "Exemplary determination and calculation of galactolipase to TAG-lipase activity ratio of variant #" in the Materials and Methods herein.

The determination of the ratio of the activity on phospholipids:the activity on triglycerides may be done via measuring using suitable assays at pH 8 such as Assays 1B and 3B as described herein and calculating the ratio analogous to "Exemplary determination and calculation of galactolipase to TAG-lipase activity ratio of variant #" in the Materials and Methods herein.

In an aspect of the disclosure the increased ratio of the activity on phospholipids:the activity on triglycerides is an increased ratio of the activity on PC:the activity on Triolein.

In an aspect of the disclosure the ratio of the activity on PC:the activity on Triolein is determined at pH 5.5. (E.g. Assays 1A and 3A and calculating the ratio as described herein)

In an aspect of the disclosure the ratio of the activity on PC:the activity on Triolein is determined at pH 8. (E.g. Assays 1B and 3B and calculating the ratio as described herein)

The disclosure provides a nucleic acid sequence encoding the variant polypeptide according to the disclosure, i.e. provides a nucleic acid sequence encoding the lipolytic enzyme variant of the disclosure.

The disclosure further provides a nucleic acid sequence encoding a lipolytic variant which comprises a sequence that has at least 70% sequence identity to the mature polypeptide having lipolytic activity as set out in SEQ ID NO: 2.

A nucleic acid sequence of the disclosure may comprise a polynucleotide sequence encoding a variant polypeptide of the disclosure which has at least 60%, 70%, 75%, 80%, 85%, 90%, 95%, 96%, 97%, 98%, or 99% sequence identity to the mature polypeptide having lipolytic activity as set out in SEQ ID NO: 2.

In an aspect, the nucleic acid sequence of the disclosure comprises a polynucleotide sequence encoding a variant polypeptide of the disclosure which has at least 70%, 75%, 80%, 85%, 90%, 95%, 96%, 97%, 98%, or 99% sequence identity to the mature polypeptide having lipolytic activity as set out in amino acids 34 to 304 of SEQ ID NO: 2.

The disclosure provides a nucleic acid construct comprising the nucleic acid sequence of the disclosure operably linked to one or more control sequences capable of directing the expression of a lipolytic enzyme in a suitable expression host.

The disclosure provides a recombinant host cell comprising a recombinant expression vector comprising the nucleic acid construct of the disclosure.

The disclosure provides a method for producing a lipolytic polypeptide variant according to the disclosure comprising cultivating the host cell of the disclosure under conditions conducive to production of the lipolytic enzyme variant and recovering the lipolytic enzyme variant.

The method to produce the lipolytic polypeptide variant according to this disclosure includes a method to produce all variants described herein.

The term "complementary strand" can be used interchangeably with the term "complement". The complementary strand of a nucleic acid can be the complement of a coding strand or the complement of a non-coding strand. When referring to double-stranded nucleic acids, the complement of a nucleic acid encoding a polypeptide refers to the complementary strand of the strand encoding the amino acid sequence or to any nucleic acid molecule containing the same. Typically, the reverse complementary strand is intended.

The term "control sequence" can be used interchangeably with the term "expression-regulating nucleic acid sequence". The term as used herein refers to nucleic acid sequences necessary for and/or affecting the expression of an operably linked coding sequence in a particular host organism or in vitro. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, leader, signal peptide, propeptide, prepropeptide, or enhancer sequences; Shine-Dalgarno sequence, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either endogenous or heterologous to a host cell. Each control sequence may be native or foreign to the nucleic acid sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

The term "derived from" also includes the terms "originated from," "obtained from," "obtainable from," "isolated from," and "created from," and generally indicates that one specified material find its origin in another specified material or has features that can be described with reference to another specified material. As used herein, a substance (e.g., a nucleic acid molecule or polypeptide) "derived from" a microorganism preferably means that the substance is native to that microorganism.

As used herein, the term "endogenous" refers to a nucleic acid or amino acid sequence naturally occurring in a host cell.

The term "expression" includes any step involved in the production of the polypeptide including, but not limited to, transcription, post transcriptional modification, translation, post-translational modification, and secretion.

An "expression vector" comprises a polynucleotide coding for a polypeptide, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon.

A "host cell" as defined herein is an organism suitable for genetic manipulation and one which may be cultured at cell densities useful for industrial production of a target product, such as a polypeptide according to the present disclosure. A host cell may be a host cell found in nature or a host cell derived from a parent host cell after genetic manipulation or classical mutagenesis. Advantageously, a host cell is a recombinant host cell.

A host cell may be a prokaryotic, archaebacterial or eukaryotic host cell. A prokaryotic host cell may be, but is not limited to, a bacterial host cell. A eukaryotic host cell may be, but is not limited to, a yeast, a fungus, an amoeba, an alga, a plant, an animal cell, such as a mammalian or an insect cell.

The term "heterologous" as used herein refers to nucleic acid or amino acid sequences not naturally occurring in a host cell. In other words, the nucleic acid or amino acid sequence is not identical to that naturally found in the host cell.

The term "hybridization" means the pairing of substantially complementary strands of oligomeric compounds, such as nucleic acid compounds.

Hybridization may be performed under low, medium or high stringency conditions. Low stringency hybridization conditions comprise hybridizing in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency hybridization conditions comprise hybridizing in 6×SSC at about 45° C., followed by one or more washes in 0.2×SSC, 0.1% SDS at 60° C., and high stringency hybridization conditions comprise hybridizing in 6×SSC at about 45° C., followed by one or more washes in 0.2×SSC, 0.1% SDS at 65° C.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein.

A "peptide" refers to a short chain of amino acid residues linked by peptide (amide) bonds. The shortest peptide, a dipeptide, consists of 2 amino acids joined by single peptide bond.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, as a result of the degeneracy of the genetic code, a multitude of nucleotide sequences encoding a given polypeptide may be produced.

An "enzyme" is a polypeptide that catalyzes a chemical reaction.

An "isolated nucleic acid fragment" is a nucleic acid fragment that is not naturally occurring as a fragment and would not be found in the natural state.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

The lipolytic enzyme variant according to the disclosure can be recovered and purified from recombinant cell cultures by methods known in the art (Protein Purification Protocols, Methods in Molecular Biology series by Paul Cutler, Humana Press, 2004).

The lipolytic enzyme variant includes naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present disclosure may be glycosylated or may be non-glycosylated. In addition, polypeptides of the disclosure may also include an initial modified methionine residue, in some cases as a result of host-mediated processes.

In the disclosure, a lipolytic polypeptide variant may be provided in the form of pre-polypeptide variant or (mature) polypeptide variant. A corresponding nucleic acid sequence may also be provided, i.e. a polynucleotide that encodes a pre-lipolytic polypeptide variant or a (mature) lipolytic polypeptide variant may be provided.

The term "nucleic acid construct" is herein referred to as a nucleic acid molecule, either single-or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

The term "promoter" is defined herein as a DNA sequence that is bound by RNA polymerase and directs the polymerase to the correct downstream transcriptional start site of a nucleic acid sequence to initiate transcription. A promoter may also comprise binding sites for regulators.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. The term "recombinant" is synonymous with "genetically modified" and "transgenic".

The terms "sequence identity" or "sequence homology" are used interchangeably herein. For the purpose of this disclosure, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleotides/bases or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this disclosure the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the disclosure is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labelled in the output of the program as "longest-identity".

The nucleic acid and protein sequences of the present disclosure can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the disclosure. BLAST protein searches can be performed with the XBLAST program, score=50, wordlength=3 to obtain amino acid sequences homologous to protein molecules of the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.gov.

As indicated above the variant polypeptide according to the disclosure may be an isolated, substantially pure, pure, recombinant or synthetic polypeptide.

In an embodiment, the variant polypeptide according to the disclosure is a non-naturally occurring polypeptide.

A "pure enzyme" is synonymous to "pure polypeptide" and means a polypeptide that is removed from at least one component, e.g. other polypeptide material, with which it is naturally associated. The polypeptide may be free of any other impurities. The polypeptide may be at least 50% pure, e.g., at least 60% pure, at least 70% pure, at least 75% pure, at least 80% pure, at least 85% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

The term "substantially pure" with regard to polypeptides refers to a polypeptide preparation which contains at the most 50% by weight of other polypeptide material. The polypeptides disclosed herein are preferably in a substantially pure form. In particular, it is preferred that the polypeptides disclosed herein are in "essentially pure form", i.e. that the polypeptide preparation is essentially free of other polypeptide material. Optionally, the polypeptide may also be essentially free of non-polypeptide material such as nucleic acids, lipids, media components, and the like. Herein, the term "substantially pure polypeptide" is synonymous with the terms "isolated polypeptide" and "polypeptide in isolated form". The term "substantially pure" with regard to polynucleotide refers to a polynucleotide preparation which contains at the most 50% by weight of other polynucleotide material. The polynucleotides disclosed herein are preferably in a substantially pure form. In particular, it is preferred that the polynucleotide disclosed herein are in "essentially pure form", i.e. that the polynucleotide preparation is essentially free of other polynucleotide material. Optionally, the polynucleotide may also be essentially free of non-polynucleotide material such as polypeptides, lipids, media components, and the like. Herein, the term "substantially pure polynucleotide" is synonymous with the terms "isolated polynucleotide" and "polynucleotide in isolated form".

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 1, but still encoding the polypeptide according to the disclosure.

As used herein, the terms "variant", "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

A polypeptide according to the present disclosure may be encoded by any suitable polynucleotide sequence. Typically, a polynucleotide sequence is codon optimized, or a codon pair optimized sequence for expression of a polypeptide as disclosed herein in a particular host cell. The polynucleotides according to the disclosure may be optimized in their codon use, preferably according to the methods described in WO2006/077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

A polypeptide of the disclosure may be encoded by a polynucleotide sequence that comprises appropriate control sequences and/or signal sequences, for example for secretion.

A polypeptide of the disclosure may be encoded by a polynucleotide that hybridizes under medium stringency, preferably under high stringency conditions to the complementary strand of the mature polypeptide coding sequence of SEQ ID NO: 2 (or the corresponding wild-type sequence or a sequence codon optimized or codon pair optimized for expression in a heterologous organism, such as a *Bacillus*, for example *Bacillus subtilis*).

A polypeptide of the disclosure may also be encoded by a nucleic acid that has at least 80%, 85%, 90%, 91%, 92%, 93%, 94%, 95%, 96%, 97%, 98%, 99% or 100% identity to a mature polypeptide coding sequence of SEQ ID NO: 2 (or the corresponding wild-type sequence or a sequence codon optimized or codon pair optimized for expression in a heterologous organism, such as a *Bacillus*, for example *Bacillus subtilis*).

A polypeptide of the disclosure may also be a variant of a mature polypeptide of SEQ ID NO: 1, comprising a substitution, deletion and/or insertion at one or more positions of the mature polypeptide SEQ ID NO: 1. A variant of the mature polypeptide of SEQ ID NO: 1 may be an amino acid sequence that differs in 1, 2, 3, 4, 5, 6, 7, 8, 9, 10, 11 or 12 amino acids from the amino acids of the mature polypeptide of SEQ ID NO: 1.

In one embodiment, the present disclosure features a biologically active fragment of a polypeptide as disclosed herein.

Biologically active fragments of a polypeptide of the disclosure include polypeptides comprising amino acid sequences sufficiently identical to or derived from the amino acid sequence of the lipolytic enzyme variant, which include fewer amino acids than the full-length protein but which exhibits at least one biological activity of the corresponding full-length protein. Typically, biologically active fragments comprise a domain or motif with at least one activity of the lipolytic enzyme variant. A biologically active fragment may for instance comprise a catalytic domain. A biologically active fragment of a protein of the disclosure can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the disclosure.

The disclosure also features nucleic acid fragments which encode the above biologically active fragments of the lipolytic enzyme variant.

A polypeptide according to the present disclosure may be a fusion protein. Techniques for producing fusion polypeptides are known in the art, and include ligating the coding sequences encoding the polypeptides so that they are in frame. Expression of the fused polypeptide is under control of the same promoter(s) and terminator. The hybrid polypeptides may comprise a combination of partial or complete polypeptide sequences obtained from at least two different polypeptides wherein one or more may be heterologous to a host cell. Such fusion polypeptides from at least two different polypeptides may comprise a binding domain from one polypeptide, operably linked to a catalytic domain from a second polypeptide. Examples of fusion polypeptides and signal sequence fusions are for example as described in WO2010/121933, WO2013/007820 and WO2013/007821.

A polypeptide of the disclosure may be a naturally occurring polypeptide or a genetically modified or recombinant polypeptide.

A polypeptide of the disclosure may be purified. Purification of proteins is known to a skilled person in the art.

The term "enzymatic activity", sometimes also referred to as "catalytic activity" or "catalytic efficiency", is generally known to the person skilled in the art and refers to the conversion rate of an enzyme and is usually expressed by means of the ratio $k_{kat}/K_M$, wherein $k_{kat}$ is the catalytic constant (also referred to as turnover number) and the $K_M$ value corresponds to the substrate concentration, at which the reaction rate lies at half its maximum value. Alternatively, the enzymatic activity of an enzyme can also be specified by the specific activity (µmol of converted substrate×mg$^{-1}$×min$^{-1}$; cf. above) or the volumetric activity (µmol of converted substrate×mV×min$^{-1}$; cf. above).

Reference can also be made to the general literature such as Structure and Mechanism in Protein Science: A guide to enzyme catalysis and protein folding, Alan Fersht, W.H. Freeman, 1999; Fundamentals of Enzyme Kinetics, Athel Cornish-Bowden, Wiley-Blackwell 2012 and Voet et al., "Biochemie" [Biochemistry], 1992, VCH-Verlag, Chapter 13, pages 331-332 with respect to enzymatic activity.

There are several ways of inserting a nucleic acid sequence into a nucleic acid construct or an expression vector which are known to a skilled person in the art, see for instance Sambrook & Russell, *Molecular Cloning: A Laboratory Manual, 3rd Ed.*, CSHL Press, Cold Spring Harbor, N.Y., 2001. It may be desirable to manipulate a nucleic acid sequence encoding a polypeptide of the present disclosure with control sequences, such as promoter and terminator sequences.

A promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter. An inducible promoter may be, for example, a starch inducible promoter.

Suitable promoters will be known to the skilled person. In a specific embodiment, promoters are preferred that are capable of directing a high expression level of the polypeptides according to the disclosure in a fungus or yeast. Such promoters are known in the art.

A variety of promoters can be used that are capable of directing transcription in the host cells of the disclosure. Preferably the promoter sequence is derived from a highly expressed gene. Strong constitutive promoters are well known and an appropriate one may be selected according to the specific sequence to be controlled in the host cell. Examples of preferred highly expressed genes from which promoters are preferably derived and/or which are comprised in preferred predetermined target loci for integration of expression constructs. Examples of suitable promotors are listed in WO 2009/106575, including examples of suitable promotors in filamentous fungi. All of the promoters mentioned therein are readily available in the art.

Any terminator which is functional in a cell as disclosed herein may be used, which are known to a skilled person in the art. Examples of suitable terminator sequences in filamentous fungi include terminator sequences of a filamentous fungal gene, for example those listed in WO 2009/106575.

The disclosure also relates to a vector which comprises a nucleic acid of the disclosure, said vector comprises at least an autonomous replication sequence and a nucleic acid as described herein.

The vector may be any vector (e.g. a plasmid or a virus), which can be conveniently subjected to recombinant DNA procedures. The choice of the vector will typically depend on the compatibility of the vector with the host cell into which the vector is to be introduced. Preferably, the vector is a plasmid. The vector may be a linear or a closed circular plasmid. The vector may further comprise a, preferably non-selective, marker that allows for easy determination of the vector in the host cell. Suitable markers include GFP and DsRed. The chance of gene conversion or integration of the vector into the host genome is preferably minimized. The vector according to the disclosure may be an extra-chromosomal vector. Such a vector preferably lacks significant regions of homology with the genome of the host to minimize the chance of integration into the host genome by homologous recombination. The person skilled in the art knows how to construct a vector with minimal chance of integration into the genome. This may be achieved by using control sequences, such as promoters and terminators, which originate from another species than the host species.

Other ways of reducing homology are by modifying codon usage and introduction of silent mutations. The person skilled in the art knows that the type of host cell, the length of the regions of homology to the host cell genome present in the vector, and the percentage of homology between said regions of homology in the vector and the host chromosome will determine whether and in which amount the vector will integrate into the host cell genome.

The autonomous replication sequence may be any suitable sequence available to the person skilled in the art that allows for plasmid replication that is independent of chromosomal replication.

The origin of replication may be any plasmid replicator mediating autonomous replication that functions in a cell.

The term "origin of replication" or "plasmid replicator" is defined herein as a nucleotide sequence that enables a plasmid or vector to replicate in vivo. Examples of bacterial origins of replication are the origins of replication of plasmids pBR322, pUC19, pACYC177, and pACYC184 permitting replication in *E. coli*, RSF1010 permitting replication in *Pseudomonas* is described, e.g., by F. Heffron et al., in Proc. Nat'l Acad. Sci. USA 72(9):3623-27 (September 1975), and pUB110, pE194, pTA1060, and pAMf31 permitting replication in *Bacillus*.

Preferably, the autonomous replication sequence used in filamentous fungi is the AMA1 replicon (Gems et al., 1991 Gene. 98(1):61-7). Telomeric repeats may also result in autonomous replication (In vivo linearization and autonomous replication of plasmids containing human telomeric DNA in *Aspergillus nidulans*, Aleksenko et al. Molecular and General Genetics MGG, 1998—Volume 260, Numbers 2-3, 159-164, DOI: 10.1007/s004380050881). CEN/ARS sequences and 3μ vector sequences from yeast may also be suitable.

A vector or expression construct for a given host cell may thus comprise the following elements operably linked to each other in a consecutive order from the 5'-end to 3'-end relative to the coding strand of the sequence encoding the compound of interest or encoding a compound involved in the synthesis of the compound of interest: (1) a promoter sequence capable of directing transcription of a nucleic acid of the disclosure; (2) optionally a sequence to facilitate the translation of the transcribed RNA, for example a ribosome binding site (also indicated as Shine Delgarno sequence) in prokaryotes, or a Kozak sequence in eukaryotes (3) optionally, a signal sequence capable of directing secretion of the lipolytic enzyme variant encoded by the nucleic acid of the disclosure from the given host cell into a culture medium; (4) a nucleic acid of the disclosure, as described herein; and preferably also (5) a transcription termination region (terminator) capable of terminating transcription downstream of the nucleic acid of the disclosure. The vector may comprise these and/or other control sequences as described herein.

Downstream of a nucleic acid of the disclosure there may be a 3'-untranslated region containing one or more transcription termination sites (e. g. a terminator, herein also referred to as a stop codon). The origin of the terminator is not critical. The terminator can, for example, be native to the DNA sequence encoding the polypeptide. However, preferably a bacterial terminator is used in bacterial host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a start codon, usually AUG (or ATG), but there are also alternative start codons, such as for example GUG (or GTG) and UUG (or TTG), which are used in prokaryotes. Also a stop or translation termination codon is appropriately positioned at the end of the polypeptide to be translated.

Enhanced expression of a lipolytic enzyme variant of the disclosure may also be achieved by the selection of homologous and heterologous regulatory regions, e. g. promoter, secretion leader and/or terminator regions, which may serve to increase expression and, if desired, secretion levels of the protein of interest from the expression host and/or to provide for the inducible control of the expression of a compound of interest or a compound involved in the synthesis of a compound of interest.

The vector comprising at least an autonomous replication sequence and a nucleic acid of the disclosure, also referred to herein as "vector (or expression vector) of the disclosure" can be designed for expression of the nucleic acid in a prokaryotic or a eukaryotic cell. For example, a lipolytic enzyme variant of the disclosure can be produced in bacterial cells such as *E. coli* or Bacilli, insect cells (using baculovirus expression vectors), fungal cells, such as yeast cells, or mammalian cells. Suitable host cells are discussed herein and further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

In order to identify and select cells which harbour a nucleic acid and/or vector of the disclosure, a gene that encodes a selectable marker (e.g., resistance to antibiotics) is optionally introduced into the vector and/or host cells along with the nucleic acid of the disclosure. Preferred selectable markers include, but are not limited to those which confer resistance to drugs or which complement a defect in the host cell. The person skilled in the art knows how choose and apply such markers. Examples of suitable markers are listed in WO 2009/106575.

Expression of proteins in prokaryotes is often carried out with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

The present disclosure also provides a host cell comprising a nucleic acid or an expression vector as disclosed herein. A suitable host cell may be a mammalian, insect, plant, fungal, or algal cell, or a bacterial cell.

The host cell may be a prokaryotic cell. In an aspect, the prokaryotic host cell is a bacterial cell. Examples of bacterial cells are listed in WO 2009/106575.

According to an embodiment, the host cell according to the disclosure is a eukaryotic host cell. Preferably, the eukaryotic cell is a mammalian, insect, plant, fungal, or algal cell. Examples of eukaryotic host cell are listed in WO 2009/106575.

The eukaryotic cell may be a fungal cell, for example a yeast cell, such as a cell of the genus *Candida, Hansenula, Kluyveromyces, Pichia, Saccharomyces, Schizosaccharomyces*, or *Yarrowia*. More specifically, a yeast cell may be from *Kluyveromyces lactis, Saccharomyces cerevisiae, Hansenula polymorpha, Yarrowia lipolytica* and *Pichia pastoris, Candida krusei*.

Preferred filamentous fungal cells belong to a species of an *Acremonium, Aspergillus, Chrysosporium, Myceliophthora, Penicillium, Talaromyces, Rasamsonia, Thielavia, Fusarium* or *Trichoderma* genus, and most preferably a species of *Aspergillus niger, Acremonium alabamense, Aspergillus awamori, Aspergillus foetidus, Aspergillus sojae, Aspergillus fumigatus, Talaromyces emersonii, Rasamsonia emersonii, Aspergillus oryzae, Chrysosporium lucknowense, Fusarium oxysporum, Myceliophthora ther-* mophila, *Trichoderma reesei*, *Thielavia terrestris* or *Penicillium chrysogenum*. A more preferred filamentous fungal host cell belongs to the genus *Aspergillus*, more preferably the host cell belongs to the species *Aspergillus niger*. When the host cell according to the disclosure is an *Aspergillus niger* host cell, the host cell preferably is CBS 513.88, CBS124.903 or a derivative thereof.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), Agricultural Research Service Patent Culture Collection, Northern Regional Research Center (NRRL), and All-Russian Collection of Microorganisms of Russian Academy of Sciences, (abbreviation in Russian—VKM, abbreviation in English—RCM), Moscow, Russia. Useful strains in the context of the present disclosure may be *Aspergillus niger* CBS 513.88, CBS124.903, *Aspergillus oryzae* ATCC 20423, IFO 4177, ATCC 1011, CBS205.89, ATCC 9576, ATCC14488-14491, ATCC 11601, ATCC12892, *P. chrysogenum* CBS 455.95, *P. chrysogenum* Wisconsin54-1255 (ATCC28089), *Penicillium citrinum* ATCC 38065, *Penicillium chrysogenum* P2, *Thielavia terrestris* NRRL8126, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Myceliophthora thermophila* C1, Garg 27K, VKM-F 3500 D, *Chrysosporium lucknowense* C1, Garg 27K, VKM-F 3500 D, ATCC44006 and derivatives thereof.

A host cell may be a recombinant or transgenic host cell. The host cell may be genetically modified with a nucleic acid construct or expression vector as disclosed herein with standard techniques known in the art, such as electroporation, protoplast transformation or conjugation for instance as disclosed in Sambrook & Russell, *Molecular Cloning: A Laboratory Manual*, 3rd Ed., CSHL Press, Cold Spring Harbor, N.Y., 2001.

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

The disclosure provides a method of producing a lipolytic polypeptide variant, which method comprises:
a) selecting a polypeptide having lipolytic activity;
b) substituting at least one amino acid residue corresponding to any of 113, 122, 138, 141, 179, 282, 284, 286, 295,
said positions being defined with reference to SEQ ID NO: 2;
c) optionally substituting one or more further amino acids as defined in b);
d) preparing the variant resulting from steps a)-c);
e) determining a property of the variant; and
f) selecting a variant having an altered property in comparison with a reference polypeptide having lipolytic activity measured under the same conditions, thereby to produce a lipolytic polypeptide variant.

The disclosure provides a method of producing a lipolytic polypeptide variant, which method comprises:
a) selecting a polypeptide having lipolytic activity;
b) substituting at least one amino acid residue corresponding to any of 113, 122, 138, 141, 179, 282, 284, 286, 295,
said positions being defined with reference to SEQ ID NO: 2;
c) optionally substituting one or more further amino acids as defined in b);
d) preparing the variant resulting from steps a)-c);
e) determining a property of the variant; and
f) selecting a variant having an altered property in comparison with a reference polypeptide having lipolytic activity, thereby to produce a lipolytic polypeptide variant, wherein the altered property includes an increased ratio of the activity on polar lipids:activity on non-polar lipids as compared to the reference polypeptide having lipolytic activity measured under the same conditions.

The disclosure provides a method of producing a lipolytic polypeptide variant, wherein in step b) the substitution, when aligned with the amino acid sequence as set out in SEQ ID NO: 2, comprises one or more of

| |
|---|
| I113H |
| I113L |
| I113N |
| I113R |
| I113T |
| L122A |
| L122M |
| H138E |
| H138S |
| F141M |
| F141Y |
| V179L |
| V179M |
| V179S |
| L282E |
| L282F |
| L282K |
| L282M |
| L282N |
| L282R |
| L282S |
| L282T |
| I284A |
| I284D |
| I284E |
| I284M |
| I284N |
| I284P |
| I284Q |
| I284S |
| I284T |
| A286L |
| D295E |
| D295G |
| D295N |
| D295S | said positions being defined with reference to SEQ ID NO: 2,
and wherein the variant has one or more altered properties as compared with a reference polypeptide having lipolytic activity.

The disclosure provides a composition comprising the variant polypeptide according to the disclosure or obtainable by the method according to the disclosure and one or more components selected from the group consisting of milk powder, gluten, granulated fat, an additional enzyme, an amino acid, a salt, an oxidant, a reducing agent, an emulsifier, sodium stearoyl lactylate, calcium stearoyl lactylate, polyglycerol esters of fatty acids and diacetyl tartaric acid esters of mono- and diglycerides, a gum, a flavour, an acid, a starch, a modified starch, a humectant and a preservative.

A composition includes a pre-mix. The term "pre-mix" is defined herein to be understood in its conventional meaning, i.e. as a mix of baking agents, generally including flour, which may be used not only in industrial bread-baking plants/facilities, but also in retail bakeries. The pre-mix according to the disclosure may be prepared by mixing the lipolytic polypeptide variant according to the disclosure polypeptide with a suitable carrier such as flour (e.g. wheat flour, corn flour and/or rice flour), starch, maltodextrin or a salt. The pre-mix may contain additives as mentioned herein.

Additives are in most cases added in powder form. Suitable additives include oxidants (including ascorbic acid, bromate and azodicarbonamide (ADA), reducing agents (including L-cysteine), emulsifiers (including without limitation mono- and diglycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), propylene glycol monostearate (PGMS), lecithin), gums (including guargum and xanthangum), flavours, acids (including citric acid, propionic acid), starches, modified starches, humectants (including glycerol) and preservatives.

In a composition according to the disclosure the additional enzyme is selected from a further lipolytic enzyme; an amylase such as an alpha-amylase, for example a fungal alpha-amylase (which may be useful for providing sugars fermentable by yeast), a beta-amylase; a glucanotransferase; a peptidase in particular, an exopeptidase (which may be useful in flavour enhancement); a transglutaminase; a cellulase; a hemicellulase, in particular a pentosanase such as xylanase (which may be useful for the partial hydrolysis of pentosans, more specifically arabinoxylan, which increases the extensibility of the dough); a protease (which may be useful for gluten weakening in particular when using hard wheat flour); a protein disulfide isomerase, e.g., a protein disulfide isomerase as disclosed in WO 95/00636; a glycosyltransferase; a peroxidase (which may be useful for improving the dough consistency); a laccase; an oxidase, such as an hexose oxidase, a glucose oxidase, aldose oxidase, pyranose oxidase; a lipoxygenase; L-amino acid oxidase (which may be useful in improving dough consistency) and an asparaginase.

In an embodiment of the composition according to the disclosure the additional enzyme is a further lipolytic enzyme, i.e. an enzyme that hydrolyses triacylglycerol and/or galactolipid and/or phospholipids.

The further lipolytic enzyme may be a lipolytic enzyme as described in WO2009/106575, such as the commercial product Panamore®, product of DSM.

The further lipolytic enzyme may be a mammalian phospholipase such as pancreatic PLA2, e.g. bovine or porcine PLA2 such as the commercial product Lecitase 10L (porcine PLA2, product of Novozymes A/S).

The further lipolytic enzyme may be from *Fusarium*, e.g. *F. oxysporum* phospholipase A1 (WO 1998/026057), *F. venenatum* phospholipase A1 (described in WO 2004/097012 as a phospholipase A2 called FvPLA2), from Tuber, e.g. *T. borchii* phospholipase A2 (called TbPLA2, WO 2004/097012).

The further lipolytic enzyme may be as described in WO 2000/032758 or WO 2003/060112. Panamore®, Lipopan® F, Lipopan® 50 and Lipopan® S are commercialised to standardised lipolytic activity, using a measurement of DLU for Panamore® from DSM and a measurement of LU for the Lipopan® family from Novozymes. DLU is defined as the amount of enzyme needed to produce 1 micromol/min of p-nitrophenol from p-nitrophenyl palmitate at pH 8.5 at 37° C., while LU is defined as the amount of enzyme needed to produce 1 micromol/min of butyric acid from tributyrin at pH 7 at 30° C. The further lipolytic enzyme may be used at 2-850 DLU/kg flour or at 50-23500 LU/kg flour. The further enzyme may be used at 14 DLU to 164 DLU/kg flour, in an aspect 27-77 DLU/kg flour.

In an embodiment of the composition according to the disclosure the further lipolytic enzyme is a lipolytic enzyme having at least 60% identity to the amino acid sequence as set out in amino acids 34 to 304 of SEQ ID NO 2, in an aspect the further lipolytic enzyme is a lipolytic enzyme comprising an amino acids sequence as set out in amino acids 34 to 304 of SEQ ID NO 2.

In an embodiment of the enzyme composition of the disclosure the additional enzyme is an enzyme as claimed in EP0869167B1.

In an embodiment of the composition according to the disclosure the additional enzyme is an alpha-amylase having at least 70% identity to the amino acid sequence as set out in SEQ ID NO: 4, in an aspect the additional enzyme is an alpha-amylase comprising an amino acid sequence as set out in SEQ ID NO: 4.

In an embodiment of the composition according to the disclosure comprises a lipolytic enzyme variant according to the disclosure and an alpha-amylase having at least 70% identity to the amino acid sequence as set out in SEQ ID NO 4.

In an embodiment of the composition according to the disclosure the additional enzyme is an amylase having at least 70% identity to the amino acid sequence as set out in SEQ ID NO 5, in an aspect the additional enzyme is an amylase comprising an amino acid sequence as set out in SEQ ID NO: 5.

In an embodiment of the composition according to the disclosure comprises a lipolytic enzyme variant according to the disclosure and an amylase having at least 70% identity to the amino acid sequence as set out in SEQ ID NO: 5.

In an aspect of the enzyme composition according to the disclosure the additional enzyme is an enzyme as described in WO 9943794, in particular as claimed in EP1058724B1.

In an embodiment of the composition according to the disclosure the additional enzyme is an amylase having an amino acid sequence at least 70% identical to the amino acid sequence as set out in SEQ ID NO: 6, in an aspect the additional enzyme is an amylase comprising an amino acid sequence as set out in SEQ ID NO: 6.

In an embodiment of the composition according to the disclosure comprises a lipolytic enzyme variant according to the disclosure and an amylase having at least 70% identity to the amino acid sequence as set out in SEQ ID NO: 6.

In an embodiment of the composition according to the disclosure the additional enzyme is an amylase having an amino acid sequence at least 70% identical to the amino acid sequence as set out in SEQ ID NO: 7, in an aspect the additional enzyme is an amylase comprising an amino acid sequence as set out in SEQ ID NO: 7.

In an embodiment of the composition according to the disclosure comprises a lipolytic enzyme variant according to the disclosure and an amylase having at least 70% identity to the amino acid sequence as set out in SEQ ID NO: 7.

The disclosure provides a composition comprising the variant polypeptide according to the disclosure or obtainable by the method according to the disclosure and a hemicellulase, such as a xylanase.

The disclosure provides a composition comprising the variant polypeptide according to the disclosure or obtainable by the method according to the disclosure and DATEM.

The disclosure provides a use of the variant polypeptide according to the disclosure, or of the composition according to the disclosure, in the production of a food product, preferably in the production of a dough and/or a baked product.

Use of the Lipolytic Enzyme in Industrial Processes

The disclosure also relates to the use of the lipolytic enzyme variant according to the disclosure in a number of industrial processes. Despite the long-term experience obtained with these processes, the lipolytic enzyme variant according to the disclosure features a number of significant advantages over the enzymes currently used. Depending on the specific application, these advantages can include aspects like lower production costs, higher specificity towards the substrate, less antigenic, less undesirable side activities, higher yields when produced in a suitable microorganism, more suitable pH and temperature ranges, better tastes of the final product as well as food grade and kosher aspects.

Preferably the lipolytic enzyme variant according to the disclosure can be used in the food industry, more preferably in food manufacturing.

Use in Industrial Applications Bakery Applications

An example of an industrial application of the lipolytic enzyme variant according to the disclosure in food is its use in baking applications to improve properties of a dough and or a baked product. It has been found that the lipolytic enzyme variants according to the disclosure can act upon several types of lipids, ranging from glycerides (e.g. triglycerides), phospholipids, and/or glycolipids, such as galactolipids, which are relevant in bakery applications. This is advantageous when used as a replacer of chemical emulsifiers in dough.

The use of the lipolytic enzyme variant according to the disclosure in baking applications modifies the natural flour lipids. This may result in improved stabilization of the dough. It may ensure a more stable dough in case of over-proofing, a larger loaf volume, and/or improved crumb structure. An improved crumb structure includes that the crumb structure may become more uniform and with smaller crumb cells, the crumb texture may become silkier and/or the crumb colour may appear to be whiter. The use of the lipolytic enzyme variant according to the disclosure in the baking industry preferably reduces the need for addition of emulsifiers like DATEM, CSL, PGME, PGE and/or SSL that otherwise are commonly added to dough for example to stabilise it.

Dough

The term "dough" is defined herein as a mixture of flour and other ingredients. In one aspect the dough is firm enough to knead or roll. The dough may be fresh, frozen, prepared or parbaked. The preparation of frozen dough is described by Kulp and Lorenz in Frozen and Refrigerated Doughs and Batters.

Dough is made using dough ingredients, which include without limitation (cereal) flour, a lecithin source including egg, water, salt, sugar, flavours, a fat source including butter, margarine, oil and shortening, baker's yeast, chemical leavening systems such as a combination of an acid (generating compound) and bicarbonate, a protein source including milk, soy flour, oxidants (including ascorbic acid, bromate and azodicarbonamide (ADA)), reducing agents (including L-cysteine), emulsifiers (including mono/di glycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), flavours, acids (including citric acid, propionic acid), starch, modified starch, gluten, humectants (including glycerol) and preservatives.

For leavened products primarily baker's yeast is used next to chemical leavening systems such as a combination of an acid (generating compound) and bicarbonate.

Cereals include maize, rice, wheat, barley, sorghum, millet, oats, rye, triticale, buckwheat, quinoa, spelt, einkorn, emmer, durum and kamut.

Dough is usually made from basic dough ingredients including (cereal) flour, such as wheat flour or rice flour, water and optionally salt. For leavened products, primarily baker's yeast is used next to chemical leavening systems such as a combination of an acid (generating compound) and bicarbonate.

The term dough herein includes a batter. A batter is a semi-liquid mixture, being thin enough to drop or pour from a spoon, of one or more flours combined with liquids such as water, milk or eggs used to prepare various foods, including cake.

The dough may be made using a mix including a cake mix, a biscuit mix, a brownie mix, a bread mix, a pancake mix and a crepe mix.

The term dough includes retarded dough, here the dough is stored at or below 5° C. during a storage period and recovered for bake off and sales.

The term retarded dough, such as frozen dough. The frozen dough is typically used for manufacturing baked products including without limitation biscuits, breads, bread sticks and croissants.

Frozen dough has several advantages for the bakery industry such as a reduction of night labour, better flexibility in production and allowing bakeries to offer a broader assortment of fresh breads.

In an aspect, the disclosure relates to the use of the lipolytic enzyme variant of the disclosure in the preparation of a frozen dough.

A further aspect includes the use of the lipolytic enzyme variant of the disclosure for improving the crumb structure of a baked product prepared from the frozen dough.

A further aspect includes the use of the lipolytic enzyme variant of the disclosure for increasing the dough stability of the frozen dough.

In an aspect the disclosure relates to the use of the lipolytic enzyme variant of the disclosure in the preparation of a baked product produced using whole-meal flour.

A further aspect includes the use of the lipolytic enzyme variant of the disclosure for improving the crumb structure of a baked product produced using whole-meal flour.

A further aspect includes the use of the lipolytic enzyme variant of the disclosure for increasing the dough stability of a baked product produced using whole-meal flour.

A further aspect includes the use of the lipolytic enzyme variant of the disclosure for increasing the dough stability of a baked product produced using whole-meal flour.

Baked Product

The term 'baked product' refers to a baked food product prepared from a dough.

Examples of baked products, whether of a white, brown or whole-meal type, which may be advantageously produced by the present disclosure include bread (in particular white, whole-meal or rye bread), typically in the form of loaves or rolls, French baguette-type bread, pastries, croissants, brioche, panettone, pasta, noodles (boiled or (stir-)fried), pita bread and other flat breads, tortillas, tacos, cakes, pancakes, cookies in particular biscuits, doughnuts, including yeasted doughnuts, bagels, pie crusts, steamed bread, crisp bread, brownies, sheet cakes, snack foods (e.g., pretzels, tortilla chips, fabricated snacks, fabricated potato crisps). The term baked product includes without limitation, bread containing from 2 to 30 wt % sugar based on total recipe weight, fruit containing bread, breakfast cereals, cereal bars, eggless cake, soft rolls and gluten-free bread.

The term baked product includes without limitation, bread containing from 2 to 30 wt % sugar based on total recipe weight, fruit containing bread, breakfast cereals, cereal bars, eggless cake, soft rolls, gluten-free bread, cake, doughnuts, brioche, hamburger buns, Brussels waffles. In an aspect the baked product is a baked product comprising sucrose such as bread containing from 2 to 30 wt % sugar based on total recipe weight, cake, doughnuts, brioche, hamburger buns, Brussels waffles. Gluten-free bread herein and herein after is bread that contains at most 20 ppm gluten. Several grains and starch sources are considered acceptable for a gluten-free diet. Frequently used sources are potatoes, rice and tapioca (derived from cassava). A baked product herein includes without limitation tin bread, loaves of bread, twists, buns, such as hamburger buns or steamed buns, chapati, rusk, dried steam bun slice, bread crumb, matzos, focaccia, melba toast, zwieback, croutons, soft pretzels, soft and hard bread, bread sticks, yeast leavened and chemically-leavened bread, laminated dough products such as Danish pastry, croissants or puff pastry products, muffins, bagels, confectionery coatings, crackers, wafers, pizza crusts, tortillas, pasta products, crepes, waffles, parbaked products. An example of a parbaked product includes, without limitation, partially baked bread that is completed at point of sale or consumption with a short second baking process. A baked product herein includes without limitation pound cake, butter cake, sponge cake, muffin, biscuit cake, roulade, genoise and chiffon cake, foam cakes.

The bread may be white or brown pan bread; such bread may for example be manufactured using a so called American style Sponge and Dough method or an American style Direct method. The bread may be a sour dough bread.

The term tortilla herein includes corn tortilla and wheat tortilla. A corn tortilla is a type of thin, flat bread, usually unleavened made from finely ground maize (usually called "corn" in the United States). A flour tortilla is a type of thin, flat bread, usually unleavened, made from finely ground wheat flour. The term tortilla further includes a similar bread from South America called arepa, though arepas are typically much thicker than tortillas. The term tortilla further includes a laobing, a pizza-shaped thick "pancake" from China and an Indian Roti, which is made essentially from wheat flour. A tortilla usually has a round or oval shape and may vary in diameter from about 6 to over 30 cm.

The disclosure provides a use wherein the use comprises replacing at least part of a chemical emulsifier in the production of a dough and/or a baked product.

Such use may be to fully replace a chemical emulsifier in the manufacturing of a dough and/or a baked product. The use may be to replace at least part of DATEM in the manufacturing of a dough and/or a baked product. The lipolytic enzyme variant according to the disclosure may be used to fully or partially replace the emulsifier DATEM. DATEM is the acronym for diacetyl tartaric acid esters of mono- and diglycerides. One of the main components in DATEM may be 1-stearoyl-3-diacetyltartryl-glycerol.

The use may be to replace at least part of SSL and/or CSL in the manufacturing of a dough and/or baked product.

The disclosure provides a use wherein the use is to the manufacturing a low chemical emulsifier or chemical emulsifier free baked product.

A low chemical emulsifier baked product is a baked product, such as bread comprising below 0.3 weight % based on flour chemical emulsifier (such as DATEM, SSL and/or CSL).

Emulsifier free indicates zero use of chemical emulsifier.

The disclosure provides a dough comprising the variant polypeptide according to the disclosure, a variant polypeptide obtainable by the method according to the disclosure or the composition according to the disclosure.

The preparation of a dough from the dough ingredients is well known in the art and includes mixing of said dough ingredients and optionally one or more moulding and leavening steps.

Preparing a dough according to the disclosure may comprise the step of combining the lipolytic enzyme variant according to the disclosure or the composition according to the disclosure or the pre-mix according to the disclosure and at least one dough ingredient. 'Combining' includes without limitation, adding the polypeptide or the composition according to the disclosure to the at least one dough ingredient, adding the at least one dough ingredient to the lipolytic enzyme variant or the composition according to the disclosure, mixing the lipolytic enzyme variant according to the disclosure and the at least one dough ingredient.

Enzymes may be combined with the at least one dough ingredient in a dry, e.g. granulated form, in a liquid form, in tablet form or in the form of a paste. Additives are in most cases added in powder form. A granulate form or agglomerated powder comprising the lipolytic enzyme variant according to the disclosure preferably has a narrow particle size distribution with more than 95% (by weight) of the particles in the range from 25 to 500 μm.

The lipolytic enzyme variant according the disclosure may be added to a dough, any ingredient from which the dough is to be made, and/or any mixture of dough ingredients from which the dough is to be made. In other words, the lipolytic enzyme variant according to the disclosure may be added in any step of the dough preparation and may be added in one, two or more steps.

The incorporation of an effective amount of the lipolytic enzyme according to the disclosure in a dough preferably reduces the need for addition of emulsifiers like DATEM and/or SSL that otherwise are commonly added to dough in order to stabilise it.

The term "effective amount" is defined herein as an amount of the lipolytic enzyme variant according to the disclosure that is sufficient for providing a measurable effect on at least one property of interest of the dough and/or baked product.

An effective amount of the composition according to the disclosure a defined herein as an amount of the composition according to the disclosure that is sufficient for providing a measurable effect on at least one property of interest of the dough and/or baked product. An effective amount for bread of the lipolytic enzyme variant includes 10-50 DLU per kg flour. An effective amount for bread of the lipolytic enzyme variant includes 400-700 DLU per kg batter (total weight of the ingredients).

DLU is defined as the amount of enzyme needed to produce 1 micromol/min of p-nitrophenol from p-nitrophenyl palmitate at pH 8.5 at 37° C. DLU may be measured analogously to as described in Assay 8A.

The disclosure provides a process for the production a dough comprising the step of combining an effective amount of the variant polypeptide according to the disclosure, an effective amount of the variant polypeptide obtainable by the method according to the disclosure or effective amount of the composition according to the disclosure with at least one dough ingredient.

If one or more additional enzymes are used in the process for the production a dough, these may be added separately or together with the lipolytic enzyme variant according to the disclosure, optionally as constituent(s) of the bread-improving and/or dough-improving composition. The additional enzymes may be dosed in accordance with established baking practices.

The disclosure provides a process for the production of a baked product, which method comprises baking the dough according to the disclosure or the dough obtained by the process of the disclosure.

The lipolytic enzyme variant and/or the composition according to the disclosure may be used in the preparation of a wide range of cakes, including shortened cakes, such as for example pound cake and butter cake, and including foam cakes, such as for example meringues, sponge cake, biscuit cake, roulade, genoise and chiffon cake. The lipolytic enzyme variant and/or the composition according to the disclosure may be used in the preparation of a muffin. Sponge cake is a highly aerated type of soft cake based on wheat flour, sugar and eggs (and optionally baking powder and fat or oil). It is often used as a base for other types of cakes and desserts. A pound cake is traditionally prepared from one pound each of flour, butter, eggs, and sugar, optionally complemented with baking powder. Sugar and egg yolk is decreased compared to pound or sponge cake and egg white content is increased.

A method to prepare a batter preferably comprises the steps of:
  a. preparing the batter of the cake by adding at least:
    i. sugar;
    ii. flour;
    iii. the lipolytic enzyme variant according to the disclosure;
    iv. at least one egg; and
    v. optionally a fat.

Fat includes, butter margarine, oil, and shortening. Optional ingredients include starch, milk components and/or emulsifier.

A method to prepare a cake according to the disclosure further comprises the step of
  b. baking the batter to yield a cake.

The person skilled in the art knows how to prepare a batter or a cake starting from dough ingredients.

The lipolytic enzyme variant according to the disclosure may be used both in regular cakes and in cakes in which the amount of eggs and/or fat has been reduced. The reduction of the amount of eggs and/or fat which is possible differs per type of cake. The person skilled in the art knows the amount of eggs and/or fat which are regularly present in cake recipes and which is dependent on the type of cake. For example, a reduction of the amount of eggs of at least 5% w/w based on total weight of the batter may be reached. For example, a reduction of the amount of eggs of at least 10% w/w may be reached, in a further aspect a reduction of at least 20% w/w of the amount of eggs may be reached. For example, a reduction of the amount of fat of at least 10% w/w based on total weight of the batter may be reached. For example a reduction of the amount of fat of at least 20% may be reached. In a further aspect a reduction of at least 30% of fat may be reached.

The lipolytic enzyme variant according to the disclosure may be used to reduce the amount of egg in the preparation of cake.

In an aspect of the method to prepare a batter, the batter comprises between 3 and 25 wt % whole egg based on the total weight of the batter. In an aspect of the method to prepare a batter, the batter comprises between 4 and 20 wt % whole egg based on the total weight of the batter. In an aspect of the method to prepare a batter, the batter comprises between 5 and 15 wt % whole egg based on the total weight of the batter. In an aspect of the method to prepare a batter, the batter comprises between 6 and 12 wt % whole egg based on the total weight of the batter.

Embodiments of the Disclosure

1. A variant polypeptide having lipolytic activity, wherein the variant has an amino acid sequence which, when aligned with the amino acid sequence as set out in SEQ ID NO: 2, comprises at least one substitution of an amino acid residue at a position corresponding to any of the positions 113, 122, 138, 141, 179, 282, 284, 286, 295,
  said positions being defined with reference to SEQ ID NO: 2,
  and wherein said variant has at least 70% identity with the mature polypeptide having lipolytic activity as set out in SEQ ID NO: 2.

2. A variant polypeptide according to embodiment 1, wherein the reference polypeptide comprises the mature lipolytic enzyme as set out in SEQ ID NO: 2.

3. A variant polypeptide according to embodiment 1 or 2, wherein the reference polypeptide is the mature lipolytic enzyme as set out in SEQ ID NO: 2.

4. A variant polypeptide according to any one of embodiments 1 to 3, wherein the mature polypeptide comprises an amino acid sequence as set out in amino acids 34 to 304 of SEQ ID NO: 2.

5. A variant polypeptide according to any one of embodiments 1 to 4, wherein the mature polypeptide has an amino acid sequence as set out in amino acids 34 to 304 of SEQ ID NO: 2.

6. A variant polypeptide according to any one of embodiments 1 to 5, wherein the variant has one or more altered properties as compared with a reference polypeptide having lipolytic activity.

7. A variant polypeptide according to any one of embodiments 1 to 6, wherein the variant demonstrates an increased ratio of the activity on polar lipids:activity on non-polar lipids as compared to the reference polypeptide having lipolytic activity measured under the same conditions.

8. A variant polypeptide according to embodiment any one of embodiments 1 to 7 which, when aligned with the amino acid sequence as set out in SEQ ID NO: 2, comprises at least one substitution of an amino acid residue at a position corresponding to any of the positions 113, 141, 179, 282, 284, 295.

9. A variant polypeptide according to any one of embodiments 1 to 8 which, when aligned with the amino acid sequence as set out in SEQ ID NO: 2, comprises at least one substitution of an amino acid residue at a position corresponding to any of the positions 113, 179, 282, 284, 295.

10. A variant polypeptide according to embodiment 7 or 8 which, when aligned with the amino acid sequence as set out in SEQ ID NO: 2, comprises at least one substitution of an amino acid residue at a position corresponding to any of the positions
113, 141, 179, 282, 284, 295,
and wherein the variant demonstrates an increased ratio of the activity on polar lipids:the activity on non-polar lipids determined at pH 5.5 as compared to the reference polypeptide having lipolytic activity.

11. A variant polypeptide according to embodiment 7 or 8 which, when aligned with the amino acid sequence as set out in SEQ ID NO: 2, comprises at least one substitution of an amino acid residue at a position corresponding to any of the positions
113, 122, 138, 141, 179, 282, 284, 286, 295
and wherein the variant demonstrates an increased ratio of the activity on polar lipids:the activity on non-polar lipids determined at pH 8 as compared to the reference polypeptide having lipolytic activity.

12. A variant polypeptide according to embodiment 7 or 8 which, when aligned with the amino acid sequence as set out in SEQ ID NO: 2, comprises at least one substitution of an amino acid residue at a position corresponding to any of the positions
113, 138, 141, 179, 282, 284, 286, 295,
and wherein the variant demonstrates an increased ratio of the activity on galactolipids:the activity on triglycerides as compared to the reference polypeptide having lipolytic activity.

13. A variant polypeptide according to embodiment 7 or 8 which, when aligned with the amino acid sequence as set out in SEQ ID NO: 2, comprises at least one substitution of an amino acid residue at a position corresponding to any of the positions
113, 122, 138, 141, 179, 282, 284, 286, 295,
and wherein the variant demonstrates an increased ratio of the activity on phospholipids:the activity on triglycerides as compared to the reference polypeptide having lipolytic activity.

14. A variant polypeptide according to any one of embodiments 1 to 13 which, when aligned with the amino acid sequence as set out in SEQ ID NO: 2, comprises one or more of the amino acid substitutions selected from

| |
|---|
| I113H |
| I113L |
| I113N |
| I113R |
| I113T |
| L122A |
| L122M |
| H138E |
| H138S |
| F141M |
| F141Y |
| V179L |
| V179M |
| V179S |
| L282E |
| L282F |
| L282K |
| L282M |
| L282N |
| L282R |
| L282S |
| L282T |
| I284A |
| I284D |
| I284E |
| I284M |
| I284N |
| I284P |
| I284Q |
| I284S |
| I284T |
| A286L |
| D295E |
| D295G |
| D295N |
| D295S. |

15. A variant polypeptide according to any one of embodiments 1 to 14, wherein the variant has an amino acid sequence which, when aligned with the amino acid sequence as set out in SEQ ID NO: 2, comprises one or more of the amino acid substitutions selected from

| |
|---|
| I113H |
| I113L |
| I113N |
| I113R |
| I113T |
| L122A |
| L122M |
| H138E |
| H138S |
| F141M |
| F141Y |
| V179L |
| V179M |
| V179S |
| L282E |
| L282F |
| L282K |
| L282M |
| L282N |
| L282R |
| L282S |
| L282T |
| I284A |
| I284D |
| I284E |
| I284M |
| I284N |
| I284P |
| I284Q |
| I284S |
| I284T |
| A286L |
| D295E |
| D295G |
| D295N |
| D295S. |

16. A nucleic acid sequence encoding a variant polypeptide according to any one of the preceding embodiments.

17. A nucleic acid construct comprising the nucleic acid sequence of embodiment 16 operably linked to one or more control sequences capable of directing the expression of a lipolytic enzyme in a suitable expression host.

18. A recombinant expression vector comprising the nucleic acid construct of embodiment 17.

19. A recombinant host cell comprising the expression vector of embodiment 18.

20. A method for producing a lipolytic polypeptide variant according to any one of embodiments 1 to 15 comprising cultivating the host cell of embodiment 19 under conditions conducive to production of the lipolytic enzyme variant and recovering the lipolytic enzyme variant.

21. A method of producing a lipolytic polypeptide variant, which method comprises:
  a) selecting a polypeptide having lipolytic activity;
  b) substituting at least one amino acid residue corresponding to any of
    113, 122, 138, 141, 179, 282, 284, 286, 295
    said positions being defined with reference to SEQ ID NO: 2;
  c) optionally substituting one or more further amino acids as defined in b);
  d) preparing the variant resulting from steps a)-c);
  e) determining the ratio of the activity on polar lipids: activity on non-polar lipids of the variant and of a reference polypeptide having lipolytic activity under the same conditions; and
  f) selecting a variant having an increased ratio of the activity on polar lipids:activity on non-polar lipids in comparison to the reference polypeptide, thereby to produce a lipolytic polypeptide variant.

22. The method according to any one of embodiments 66 to 72 wherein in step b) the substitution, when aligned with the amino acid sequence as set out in SEQ ID NO: 2, comprises one or more of

| |
|---|
| I113H |
| I113L |
| I113N |
| I113R |
| I113T |
| V179L |
| V179M |
| V179S |
| L282E |
| L282F |
| L282K |
| L282M |
| L282N |
| L282R |
| L282S |
| L282T |
| I284A |
| I284D |
| I284E |
| I284M |
| I284N |
| I284P |
| I284Q |
| I284S |
| I284T |
| D295E |
| D295G |
| D295N |
| D295S | said positions being defined with reference to SEQ ID NO: 2,
and wherein the variant has one or more altered properties as compared with a reference polypeptide having lipolytic activity.

23. A composition comprising the variant polypeptide according to any one of embodiments 1 to 15 or obtainable by the method according to 21 or 22 and one or more components selected from the group consisting of milk powder, gluten, granulated fat, an additional enzyme, an amino acid, a salt, an oxidant, a reducing agent, an emulsifier, sodium stearoyl lactylate, calcium stearoyl lactylate, polyglycerol esters of fatty acids and diacetyl tartaric acid esters of mono- and diglycerides, a gum, a flavour, an acid, a starch, a modified starch, a humectant and a preservative.

24. A composition according embodiment 24 wherein the additional enzyme is selected from a further lipolytic enzyme; an amylase such as an alpha-amylase, for example a fungal alpha-amylase, a beta-amylase; a glucanotransferase; a peptidase in particular, an exopeptidase; a transglutaminase; a cellulase; a hemicellulase, in particular a pentosanase such as xylanase; protease; a protein disulfide isomerase; a glycosyltransferase; a peroxidase; a laccase; an oxidase, such as an hexose oxidase, a glucose oxidase, aldose oxidase, pyranose oxidase; a lipoxygenase; L-amino acid oxidase and an asparaginase.

25. A pre-mix comprising flour and the variant polypeptide according to any one of embodiments 1 to 15, the variant polypeptide obtainable by the method according to embodiment 21 or 22 or the composition according to embodiment 23 or 24.

26. A use of the variant polypeptide according to any one of embodiments 1 to 15, or of the composition according to any one of embodiment 23 or 24, or of the pre-mix according to embodiment 25 in the manufacturing of a food product, preferably in the manufacturing of a dough and/or a baked product.

27. The use according to embodiment 26, wherein the use comprises replacing at least part of a chemical emulsifier in the manufacturing of a dough and/or a baked product.

28. The use according to embodiment 26, wherein the use is to fully replace a chemical emulsifier in the manufacturing of a dough and/or a baked product.

29. The use according to embodiment 27 or 28, wherein the use comprises replacing at least part of DATEM in the manufacturing of a dough and/or a baked product.

30. The use according to embodiment 27 or 28, wherein the use comprises replacing at least part of SSL and/or CSL in the manufacturing of a dough and/or baked product.

31. The use of the variant polypeptide according to any one of embodiments 1 to 15, or of the composition according to any one of embodiment 23 or 24, or of the pre-mix according to embodiment 25 in the manufacturing of a low chemical emulsifier or chemical emulsifier free baked product.

32. The use according to embodiment 31, wherein the baked product has been produced using whole-meal flour and/or whole grain.

33. The use according to any one of embodiments 26 to 32 wherein the baked product has been produced from a frozen dough.

34. The use according to embodiment 31 and/or 32 wherein the chemical emulsifier is mono- and diglycerides of fatty acids or distilled mono glycerides sodium stearoyl lactylate (SSL), calcium stearoyl lactylate (CSL), polyglycerol esters of fatty acids (PGE), propylene glycol mono esters of fatty acids (PGME), and diacetyl tartaric acid esters of mono- and diglycerides (DATEM) or lecithin.

35. The use according to any one of embodiments 26 to 34, wherein the use is to increase volume of a baked product.

36. The use according to any one of embodiments 26 to 34, wherein the use is to reduce hardness of a baked product.

37. The use according to any one of embodiments 26 to 34, wherein the use is to create a finer crumb structure of a baked product.

38 The use according to any one of embodiments 26 to 34, wherein the use is to increase stability of a dough.

39. The use according to any one of embodiments 26 to 38, wherein the baked product is bread, cake and/or pastry.

40. The use according to any one of embodiments 26 to 34, 39, wherein the use is to reduce the amount of egg in the preparation of cake.

41. A dough comprising a variant polypeptide according to any one of embodiments 1 to 15, the variant polypeptide obtainable by the method according to embodiment 21 or 22, the composition according to embodiment 23 or 24, or the pre-mix according to embodiment 25.

42. A process for preparing a dough comprising the step of combining an effective amount of the variant polypeptide according to any one of embodiments 1 to 15, an effective amount of the variant polypeptide obtainable by the method according to embodiment 21 or 22, an effective amount of the composition according to embodiment 23 or 24 or an effective amount of the pre-mix according to embodiment 25 with at least one dough ingredient.

43. A process for the production of a baked product, which method comprises baking the dough according to embodiment 41 or the dough obtained by the process of embodiment 42.

44. The process according to embodiment 43, wherein the baked product is bread, cake and/or pastry.

45. A baked product obtainable by the process according to embodiment 43 or 44, or by the use according to any one of embodiments 26 to 40.

46. A process for the production of a food product, which method comprises adding the variant polypeptide according to any one of embodiments 1 to 15, the variant polypeptide obtainable by the method according to embodiment 21 or 22, the composition according to embodiment 23 or 24 or the pre-mix according to embodiment 25 to an ingredient of a food product.

47. A process for the production of a food product, which method comprises adding an effective amount of the variant polypeptide according to any one of embodiments 1 to 15, an effective amount of the variant polypeptide obtainable by the method according to embodiment 21 or 22, an effective amount of the composition according to embodiment 23 or 24 or an effective amount of the pre-mix according to embodiment 25 to an ingredient of a food product.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present disclosure is further illustrated by the following Examples:

EXAMPLES

General Procedures and Molecular Biology Techniques

Standard molecular cloning techniques such as DNA isolation, gel electrophoresis, enzymatic restriction modifications of nucleic acids, E. coli transformation etc., were performed as described by Sambrook et al., 1989 ($2^{nd}$ ed) and 2001 ($3^{rd}$ ed), Molecular cloning: a laboratory manual, Cold Spring Harbor Laboratory Press, Cold Spring Harbor, N.Y. and Innes et al. (1990) PCR protocols, a guide to methods and applications, Academic Press, San Diego. Examples of the general design of expression vectors for gene overexpression and disruption vectors for down-regulation, transformation, use of markers, strains and selective media can be found in WO199846772, WO199932617, WO2001121779, WO2005095624, WO2006040312, EP 635574B, WO2005100573, WO2011009700, WO2012001169, WO2013135729, WO2014013073 and WO2014013074. After transformation, the direct repeats allow for the removal of the selection marker by a (second) homologous recombination event. The removal of a marker such as amdS can be done by plating on fluoro-acetamide media, resulting in the selection of marker-gene-free strains (see also "MARKER-GENE FREE" approach in EP 0 635 574). Alternatively, a marker can be removed for example using a recombinase such as detailed in WO2013135729. Using these strategies of transformation and subsequent marker removal, a marker can be used indefinitely in strain modification programs.

Strains

WT 1: This *Aspergillus niger* strain is used as a wild-type strain. This strain is deposited at the CBS Institute under the deposit number CBS 513.88.

GBA 306: The construction of GBA 306 using WT1 as starting strain has been described in detail in WO2011/009700. This GBA 306 strain has the following genotype: ΔglaA, ΔpepA, ΔhdfA, an adapted BamHI amplicon, ΔamyBII, ΔamyBI, and ΔamyA.

Biochemical Assays

Materials and Methods

The reference polypeptide used in the examples is a reference polypeptide having lipolytic activity and having an amino acid sequence as set out in amino acids 34 to 304 of SEQ ID NO: 2.

The properties of the lipolytic enzyme variants were tested using several substrates. These include the following:

Phosphatidylcholines, which may be abbreviated as PC;

Digalactosyldiglycerides, which may be abbreviated as DGDG;

Monogalactosyldiglycerides, which may be abbreviated as MGDG; and

Triacylglycerols which may be abbreviated as TAG. Triolein is applied in assays described herein as a representative of triglycerides.

para-nitrophenyl linoleate (pNP-linoleate), which may also be referred herein as an ester of C18:2 fatty acid;

para-nitrophenyl oleate (pNP-oleate), which may also be referred herein as an ester of C18:1 fatty acid;

para-nitrophenyl stearate (pNP-stearate), which may also be referred herein as an ester of C18:0 fatty acid;

para-nitrophenyl palmitate (pNP-palmitate), which may also be referred herein as an ester of C16:0 fatty acid;

para-nitrophenyl butyrate (pNP-butyrate), which may also be referred herein as an ester of C4 fatty acids;

Assay 1A Phospholipase Activity at pH 5.5

Enzymatic activity of the lipolytic enzyme variant and of the parent polypeptide (also referred as reference polypeptide) may be expressed in NEFA Units. One Unit (U) is defined as the amount of enzyme that liberates one micromole of free fatty acid per minute under the defined assay conditions.

The principle of the assay is as follows: A mix of enzyme, buffer, substrate, and calciumchloride is incubated at 37° C. for 10 minutes. The reaction is stopped by addition of an acidic solution. The amount of formed free fatty acids is subsequently determined using the principle of the NEFA kit (NEFA-HR (2) R1 Set, 434-91795, NEFA-HR (2) R2 Set, 436-91995, NEFA standard, 270-77000, all from Wako Chemicals). The principle of the NEFA method is as follows: Non-esterified fatty acid (NEFA) in the reaction sample is converted to acyl-CoA, AMP and pyrophosphoric acid (PPi) by the action of acyl-CoA synthetase (ACS), in the presence of coenzyme A (CoA) and adenosine 5-triphosphate disodium salt (ATP). Acyl-CoA is oxidized to form 2,3-trans-Enoyl-CoA and hydrogen peroxide by the action of acyl-CoA oxidase (ACOD). In the presence of peroxidase (POD), the hydrogen peroxide formed yields a blue purple pigment after quantitative oxidation condensation with 3-methyl-N-ethyl-N-(β-hydroxyethyl)-aniline (MEHA) and 4-aminoantipyrine (4-AA). The concentration of non-esterified fatty acids (NEFA) concentration is obtained by measuring absorbance of the blue purple color. NEFA standard consists of a solution of oleic acid, which is used to produce a calibration line to calculate the amount of free fatty acids. The NEFA method is performed on the Konelab Arena 30 analyzer (Thermo Scientific, Vantaa, Finland) and the intensity of the color is measured at 540 nm. The reaction sample absorbance is corrected by subtracting the absorbance of an appropriate reaction sample blank as described below.

Enzyme samples were diluted to a range between 0.05-1.5 U/mL in 0.2 M acetate buffer pH5.5. For each reaction sample and reaction sample blank glass tubes containing 50 microliter of a 0.1 M calciumchloride solution, 500 microliter substrate solution (1% (w/v) L-alpha-phosphatidylcholine (P3556, Sigma Aldrich) in 2% Triton X-100), and 250 microliter 0.2 M acetate buffer pH5.5 were prepared. These were preheated for 10 minutes in a water bath at 37° C. The reaction was started by adding 100 microliter of enzyme sample to the glass tube. 10 minutes after enzyme sample addition, 100 microliter of 2.0 M HCl was added, the tube was immediately removed from the water bath and mixed well by vortexing to terminate the reaction. For each reaction sample, a corresponding reaction sample blank was prepared by incubation of buffer, substrate, and calciumchloride at 37° C. After 10 minutes, 100 microliter of 2.0 M HCl was added, the tube was immediately removed from the water bath and mixed well by vortexing. Then 100 microliter of enzyme sample was added to the tube, and mixed well by vortexing.

Released free fatty acids were determined according to the HR Series NEFA-HR (2) kit instructions, which were made suitable for analyzer application as follows. 150 microliter of reagent NEFA-R1 was preheated for 300 seconds. Then 10 microliter of reaction sample was added, and incubation continued for 180 seconds. Subsequently 75 microliter of reagent NEFA-R2 was added and incubation continued for 270 seconds. At this moment absorbance was measured at 540 nm. The absorbance of each reaction sample was corrected by subtracting the absorbance of the corresponding reaction sample blank. The amount of non-esterified fatty acids was calculated using an oleic acid calibration line.

Assay 1B Phospholipase Activity at pH 8.0

Enzymatic activity of the lipolytic enzyme variant and of the parent polypeptide (also referred as reference polypeptide) may be expressed in NEFA Units. One Unit (U) is defined as the amount of enzyme that liberates one micromole of free fatty acid per minute under the defined assay conditions.

The principle of the assay is as follows: A mix of enzyme, buffer, substrate, and calciumchloride is incubated at 37° C. for 10 minutes. The reaction is stopped by addition of an acidic solution. The amount of formed free fatty acids is subsequently determined using the principle of the NEFA kit (NEFA-HR (2) R1 Set, 434-91795, NEFA-HR (2) R2 Set, 436-91995, NEFA standard, 270-77000, all from Wako Chemicals). The principle of the NEFA method is as follows: Non-esterified fatty acid (NEFA) in the reaction sample is converted to acyl-CoA, AMP and pyrophosphoric acid (PPi) by the action of acyl-CoA synthetase (ACS), in the presence of coenzyme A (CoA) and adenosine 5-triphosphate disodium salt (ATP). Obtained acyl-CoA is oxidized and yields 2,3-trans-Enoyl-CoA and hydrogen peroxide by the action of acyl-CoA oxidase (ACOD). In the presence of peroxidase (POD), the hydrogen peroxide formed yields a blue purple pigment after quantitative oxidation condensation with 3-methyl-N-ethyl-N-(β-hydroxyethyl)-aniline (MEHA) and 4-aminoantipyrine (4-AA). The concentration of non-esterified fatty acids (NEFA) concentration is obtained by measuring absorbance of the blue purple color. NEFA standard consists of a solution of oleic acid, which is used to produce a calibration line to calculate the amount of free fatty acids. The NEFA method is performed on the Konelab Arena 30 analyzer (Thermo Scientific, Vantaa, Finland) and the intensity of the color is measured at 540 nm. The reaction sample absorbance is corrected by subtracting the absorbance of an appropriate reaction sample blank as described below.

Enzyme samples were diluted to a range between 0.05-1.5 U/mL in 0.2 M Tris-HCl pH 8.0. For each reaction sample and reaction sample blank glass tubes containing 50 microliter of a 0.1 M calciumchloride solution, 500 microliter substrate solution (1% (w/v) L-alpha-phosphatidylcholine (P3556, Sigma Aldrich) in 2% Triton X-100), and 250 microliter 0.2 M Tris-HCl pH 8.0 were prepared. These were preheated for 10 minutes in a water bath at 37° C. The reaction was started by adding 100 microliter of enzyme sample to the glass tube. 10 minutes after enzyme sample addition, 100 microliter of 2.0M HCl was added, the tube was immediately removed from the water bath and mixed well by vortexing to terminate the reaction. For each reaction sample, a corresponding reaction sample blank was prepared by incubation of buffer, substrate, and calciumchloride at 37° C. After 10 minutes, 100 microliter of 2.0 M HCl was added, the tube was immediately removed from the water bath and mixed well by vortexing. Then 100 microliter of enzyme sample was added to the tube, and mixed well by vortexing.

Released free fatty acids were determined according to the HR Series NEFA-HR (2) kit instructions, which were made suitable for analyzer application. 150 microliter of reagent NEFA-R1 was preheated for 300 seconds. Then 10 microliter of reaction sample was added, and incubation continued for 180 seconds. Subsequently 75 microliter of reagent NEFA-R2 was added and incubation continued for 270 seconds. At this moment absorbance was measured at 540 nm. The absorbance of each reaction sample was corrected by subtracting the absorbance of the corresponding reaction sample blank. The amount of non-esterified fatty acids was determined relative to an oleic acid calibration line.

Assay 2A Galactolipase Activity at pH 5.5

As under assay 1A, except that the substrate consisted of 1% (w/v) Digalactosyldiglyceride (DGDG, plant based, from Lipid Products), in 2% Triton X-100.

Assay 2B Galactolipase Activity at pH 8.0

As under assay 1B, except that the substrate consisted of 1% (w/v) Digalactosyldiglyceride (DGDG, plant based, from Lipid Products), in 2% Triton X-100.

Assay 3A TAG-Lipase Activity at pH 5.5

As under assay 1A, except that the substrate consisted of an aqueous solution with 4.5 mM Triolein, 1.0 M NaCl, 13% (w/v) Triton X-100 (62314, Sigma Aldrich).

Assay 3B TAG-Lipase Activity at pH 8.0

As under assay 1B, except that the substrate consisted of an aqueous solution with 4.5 mM Triolein, 1.0 M NaCl, 13% (w/v) Triton X-100 (62314, Sigma Aldrich).

Assay 4A Lipolytic Activity on pNP-Linoleate at pH 5.5

Enzymatic activity of the lipolytic enzyme variant and of the parent polypeptide (also referred as reference polypeptide) may be expressed in pNP (4-nitrophenol) Units. One Unit (U) is defined as the amount of enzyme that liberates one micromole of 4-nitrophenol per minute under the conditions of the test.

The principle of the assay is as follows: For the reaction sample a mix of enzyme and substrate solution is incubated at 25° C. for 30 minutes. During the incubation time, absorbance at 348 nm ($Abs_{348\ nm}$) is measured. The initial slope (Delta $Abs_{348\ nm}$) of the linear part of the absorbance measurement of the reaction sample is corrected with the initial slope (Delta $Abs_{348\ nm}$) of an appropriate reaction sample blank as described below. A calibration line is measured as follows a mixture of buffer, and substrate solution is incubated at 25° C. for 30 minutes. During the incubation time, absorbance at 348 nm ($Abs_{348\ nm}$) is measured. For the calibration line the same volume of buffer and substrate are used as for the reaction sample but instead of enzyme 4-nitrophenol is used). For the calibration line a range of 0-10 mM 4-nitrophenol is used. The absorbance of the calibration samples is plotted against their concentration and the initial slope (Delta Abs 348 nm) of the linear part is calculated.

The activity of the enzyme is obtained by dividing the initial slope of the reaction sample by the initial slope of the calibration line. This gives the activity of the enzyme in mM/min.

Substrate solution was prepared as follows: An 8.0 mM solution of the chromogenic substrate in 2-propanol was made. Subsequently, 3.5 mL of this solution was added to 46.5 mL 100 millimol/L sodium acetate buffer pH 5.5 containing 1% Triton X-100, under vigorous stirring. Substrate was pNP-linoleate (>95% pure, from Syncom, The Netherlands).

Enzyme was diluted in 100 millimol/L sodium acetate buffer pH 5.5 containing 1% Triton X-100, such that the absorbance increase after 30 minutes is less than 1.0. Reaction was started by mixing 10 microliter of diluted enzyme sample with 240 microliter of substrate solution in a microtiter plate. 200 microliter of this mixture was added to a new microtiter plate, placed in a TECAN Infinite M1000 micro titer plate reader, temperature is kept at 25° C., and the change in absorbance of the mixture was measured for 30 minutes at 348 nm (isosbestic point of 4-nitrophenol). The reaction sample blank was prepared by adding 10 microliter of sodium acetate buffer pH 5.5 instead of enzyme sample to the substrate solution and then following the steps identical as described above for the enzyme reaction. A calibration line was produced from 4-nitrophenol dissolved in 100 millimol/L sodium acetate buffer pH 5.5 containing 1% Triton X-100.

The absorbance of the reaction samples was plotted against the time. The slope was determined over the initial linear part of the absorbance measurement. The initial slope of the reaction samples was corrected by subtracting the slope of the reaction sample blank. Subsequently activity was calculated relative to the slope of the calibration line.

Assay 4B Lipolytic Activity on pNP-Linoleate at pH 7.0
As under assay 4A, except that the buffer consisted of 100 millimol/L MOPS pH 7.0 containing 1% Triton X-100.

Assay 5A Lipolytic Activity on pNP-Oleate at pH 5.5
As under assay 4A, except that the substrate consisted of pNP-oleate (>95% pure, from Syncom, The Netherlands).

Assay 5B Lipolytic Activity on pNP-Oleate at pH 7.0
As under assay 4B, except that the substrate consisted of pNP-oleate (>95% pure, from Syncom, The Netherlands).

Assay 6A Lipolytic Activity on pNP-Stearate at pH 5.5
As under assay 4A, except that the substrate consisted of pNP-stearate (N3627, Sigma Aldrich).

Assay 6B Lipolytic Activity on pNP-Stearate at pH 7.0
As under assay 4B, except that the substrate consisted of pNP-stearate (N3627, Sigma Aldrich).

Assay 7A Lipolytic Activity on pNP-Butyrate at pH 5.5
As under assay 4A, except that the substrate consisted of pNP-butyrate (N9876, Sigma Aldrich).

Assay 7B Lipolytic Activity on pNP-Butyrate at pH 7.0
As under assay 4B, except that the substrate consisted of pNP-butyrate (N9876, Sigma Aldrich).

Assay 8A Lipolytic Activity on pNP-Palmitate at pH 8.5
As under assay 4A, except that the buffer consisted of 100 millimol/L Tris pH 8.5 containing 1% Triton X-100, and the substrate consisted of pNP-palmitate (N2752, Sigma Aldrich).

Assay 9 Lipolytic Activity pH Profile on pNP-Linoleate
As under assay 4A, except that the buffer consisted of either 100 millimol/L sodium acetate buffer pH 4.0 containing 1% Triton X-100, 100 millimol/L sodium acetate buffer pH 4.5 containing 1% Triton X-100, 100 millimol/L sodium acetate buffer pH 5.0 containing 1% Triton X-100, 100 millimol/L sodium acetate buffer pH 5.5 containing 1% Triton X-100 millimol/L, 100 millimol/L MES buffer pH 6.0 containing 1% Triton X-100, 100 millimol/L MOPS buffer pH 6.5 containing 1% Triton X-100 millimol/L, 100 millimol/L MOPS buffer pH 7.0 containing 1% Triton X-100 millimol/L, 100 millimol/L MOPS buffer pH 7.5 containing 1% Triton X-100 millimol/L, or 100 millimol/L TRIS buffer pH 8.0 containing 1% Triton X-100 millimol/L.

Determination of Altered Properties

Altered properties of lipolytic enzyme variants according to the disclosure as compared with a reference polypeptide having an amino acid sequence as set out in amino acids 34 to 304 of SEQ ID NO: 2 were obtained as follows.

Firstly, the properties of the variants and the reference polypeptide were measured as described under Assay 1A to Assay 9 above.

Secondly, from these measurements the percentages (%) listed in Tables 2 to 5 below were obtained. The way to obtain the percentages listed in the tables below is explained via an exemplary determination and calculation of galactolipase to TAG-lipase activity ratio (Table 2). The % in Tables 3 to 5 were obtained analogously.

Exemplary Determination and Calculation of Galactolipase to TAG-Lipase Activity Ratio of Variant #

The activity of variant # on Digalactosyldiglyceride (DGDG) (measured as described under Assay 2A above) was expressed as a ratio to the activity measured for the same variant on triolein (measured as described under Assay 3A above).

The reference polypeptide (having an amino acid sequence as set out in amino acids 34 to 304 of SEQ ID NO: 2) was subjected to the same experimental conditions.

If the activity of variant # would be 850 units/mL on DGDG (Assay 2A), and 1000 units/ml on triolein (Assay 3A), the ratio of activity of galactolipase to TAG-lipase for variant # would be 0.85.

If the activity of the reference polypeptide would be 600 units/mL on DGDG (Assay 2A), and 1000 units/mL on triolein (Assay 3A), then the ratio of the activity of galactolipase to TAG-lipase for the reference polypeptide would be 0.6.

This value of the reference polypeptide is then normalized to 100%.

In this exemplary calculation the galactolipase to TAG-lipase activity ratio of variant # compared with the reference polypeptide would then be (0.85/0.60)×100%=142%. 142% (for variant #) is an increase compared with 100% (for the reference polypeptide), as a result variant # is said to have an increased galactolipase to TAG-lipase activity ratio compared with the reference polypeptide. This value of 142% is thus a normalised %. In the tables in the examples normalised % are listed.

In short table 2 lists: the ratio of
[Activity of variant # in Assay 2A]:[Activity of variant # in assay 3A],
expressed as a percentage of the ratio of
[Activity of the reference polypeptide in Assay 2A]:[Activity of the reference polypeptide in Assay 3A].
The percentage thus obtained is the galactolipase to TAG-lipase activity ratio as listed in table 2.

Example 1. Design and Cloning of the Lipolytic Enzyme Variant of the Disclosure

The protein sequence (amino acid sequence) of the reference polypeptide (also referred to as parent polypeptide) having lipolytic activity is shown in amino acids 34 to 304 SEQ ID NO: 2. A codon-adapted DNA sequence for expression of the lipolytic enzyme proteins (lipolytic enzyme variants and reference polypeptide) in *Aspergillus niger* was designed containing additional BsaI type II restriction enzyme sites to enable subcloning in the *Aspergillus* expression vector pGBFIN-50 (see also FIG. 1). Codon adaptation was performed as described in WO2008/000632. The codon optimized DNA sequence for expression of the gene encoding the reference polypeptide in *A. niger* is shown in SEQ ID NO: 1.

The translational initiation sequence of the glucoamylase glaA promoter was modified into 5'-CACCGTCAAA ATG-3' (SEQ ID NO: 3) (already present in the *Aspergillus* expression vector pGBFIN-50) and an optimal translational termination sequence 5'-TAAA-3' was used in the generation of the lipolytic enzyme expression constructs (as also detailed in WO2006/077258 and WO2011/009700). The DNA sequences coding for the lipolytic enzyme variants and for the reference polypeptide of the invention were synthesized completely (DNA2.0, Menlo Park, USA) and cloned into *Aspergillus niger* expression vector pGBFIN-50 thru repetitive steps of BsaI digestion and ligation (GoldenGate cloning method (New England Biolabs), according standard procedure. The resulting vectors containing the lipolytic enzyme expression cassette (including the expression cassette for the lipolytic enzyme variants and the reference polypeptide see Table 1 below for details) under control of the glucoamylase promoter and were named pGBFINPL-00 up to pGBFINPL-51.

Subsequently, *A. niger* GBA 306 was transformed with a PCR-amplified Pgla-3'gla fragment generated using the pGBFINPL-00 up to pGBFINPL-51 vectors as template. The PCR fragment is comprising the lipolytic enzyme expression cassette under control of the glucoamylase promoter and terminator as well as the hygromycin selection marker. Alternatively, a NotI-digested and purified fragment of the pGBFINPL-00 up to pGBFINPL-51 vectors constructed, containing the lipolytic enzyme expression cassette and the hygromycin selection marker could have been used. Transformation experiments were performed with strain and methods as described in WO199846772, WO199932617, WO2011009700, WO2012001169, WO2013135729, WO2014013073 and WO2014013074 and references therein. After transformation, the protoplasts were plated onto selective regeneration medium consisting of *Aspergillus* minimal medium supplemented with 60 µg/mL Hygromycin B. After incubation for 5-10 days at 30° C., single transformants were restreaked to single colonies on PDA (Potato Dextrose Agar) supplemented with 60 µg/mL Hygromycin B. After 5-7 days growth and sporulation at 30° C., single colonies were transferred to PDA plates. Following growth for 5-7 days at 30° C. spores were isolated and used as inoculation material for shake flask fermentations.

Transformants of lipolytic enzymes named PL-00, PL-01 up to and including PL-51, were used for fermentations (see Table 1 below for details)

The amino acid changes that were introduced in the 51 lipolytic enzyme variants are listed in Table 1.

TABLE 1

Amino acid changes introduced in the parent polypeptide, wherein the parent polypeptide has an amino acid sequence as set out in amino acids 34 to 304 of SEQ ID NO: 2. Amino acids are depicted according to the single letter annotation.

| # | Amino acid change* |
|---|---|
| 00 (parent polypeptide also referred to as reference polypeptide) | none |
| 01 | Y53F |
| 02 | Y53S |
| 03 | S112T |
| 04 | I113H |
| 05 | I113L |
| 06 | I113N |
| 07 | I113R |
| 08 | I113T |
| 09 | N117D |
| 10 | N121D |
| 11 | L122A |
| 12 | L122M |
| 13 | F124L |
| 14 | H138E |
| 15 | H138S |
| 16 | F141M |
| 17 | F141Y |
| 18 | A178G |
| 19 | V179L |
| 20 | V179M |
| 21 | V179S |
| 22 | L182F |
| 23 | G200A |
| 24 | P202A |
| 25 | R203M |
| 26 | P229Q |
| 27 | P235L |
| 28 | F238L |
| 29 | L282E |
| 30 | L282F |
| 31 | L282K |
| 32 | L282M |
| 33 | L282N |
| 34 | L282R |
| 35 | L282S |
| 36 | L282T |
| 37 | I284A |
| 38 | I284D |
| 39 | I284E |
| 40 | I284F |
| 41 | I284M |
| 42 | I284N |
| 43 | I284P |
| 44 | I284Q |
| 45 | I284S |
| 46 | I284T |
| 47 | A286L |
| 48 | D295E |
| 49 | D295G |
| 50 | D295N |
| 51 | D295S |

*positions being defined with reference to SEQ ID NO: 2

Example 2. Expression of the Lipolytic Enzyme Variants and the Reference Polypeptide Using the PL-00 to PL-51 Transformants from Example 1

Fresh *A. niger* PL-00 up to PL-51 spores were prepared and used for generating lipolytic enzyme sample material by cultivation of the strains in shake flask. *A. niger* strains were precultured in 20 mL preculture medium in a 100 mL shake flask with baffle containing per liter: 100 g Corn Steep Solids (Roquette), 1 g NaH2PO4.H2O, 0.5 g MgSO4.7H2O, 10 g Glucose.H2O, 0.25 g Basildon pH5.8. After overnight growth at 34° C. and 170 rpm 10 mL of this culture was transferred to 100 mL fermentation medium in 500 mL shake flasks with baffle. Fermentation medium contains per liter: (150 g maltose, 60 g bacto-soytone, 15 g $(NH_4)_2SO_4$, 1 g $NaH_2PO_4.H_2O$, 1 g $MgSO_4.7H_2O$, 1 g L-arginine, 0.08 g Tween-80, 0.02 g Basildon, 20 g MES, pH 6.2 Cultures were grown for 2-7 days at 34° C., 170 rpm. Culture supernatants were recovered by centrifugation for 10 min at 5000×g.

Measurement of Lipolytic Activity

Enzymatic activity of the lipolytic enzyme variants and of the parent polypeptide (also referred as reference polypeptide) may be expressed in NEFA Units. One Unit (U) is defined as the amount of enzyme that liberates one micromole of free fatty acid per minute under the defined assay conditions.

The lipolytic activity of the lipolytic enzyme variants and of the parent polypeptide having lipolytic activity was demonstrated using the Assays described herein (see examples below). All lipolytic enzyme variants listed in Table 1 and the parent polypeptide showed lipolytic activity.

Example 3: Galactolipase to TAG-Lipase Activity Ratio at pH 5.5 of Variants According to the Disclosure Galactolipase to TAG-lipase activity ratio of variants as compared to the reference polypeptide was determined using the enzymes obtained in Example 2. This ratio was determined as described herein under Materials and Methods above (applying Assay 2A, Assay 3A, and "Exemplary determination and calculation of galactolipase to TAG-lipase activity ratio of variant #"). The results are listed in Table 2.

TABLE 2

Galactolipase to TAG-lipase activity ratio at pH 5.5 of variants according to the disclosure compared to the reference polypeptide. The galactolipase to TAG-lipase activity ratio of the reference polypeptide (polypeptide having an amino acid sequence as set out in amino acids 34 to 304 of SEQ ID NO: 2), was set at 100%. In the table normalised % are listed. A galactolipase to TAG-lipase activity ratio of more than 100% shows that the variant has an increased galactolipase activity compared to the reference polypeptide.

| Amino Acid Change* | galactolipase to TAG-lipase activity ratio at pH 5.5 (%) |
|---|---|
| I113N | 208% |
| I113T | 148% |
| I113H | 375% |
| I113R | 188% |
| F141Y | 207% |
| V179M | 129% |
| L282F | 123% |
| L282M | 126% |
| L282K | 167% |
| L282S | 113% |

TABLE 2-continued

Galactolipase to TAG-lipase activity ratio at pH 5.5 of variants according to the disclosure compared to the reference polypeptide. The galactolipase to TAG-lipase activity ratio of the reference polypeptide (polypeptide having an amino acid sequence as set out in amino acids 34 to 304 of SEQ ID NO: 2), was set at 100%. In the table normalised % are listed. A galactolipase to TAG-lipase activity ratio of more than 100% shows that the variant has an increased galactolipase activity compared to the reference polypeptide.

| Amino Acid Change* | galactolipase to TAG-lipase activity ratio at pH 5.5 (%) |
|---|---|
| I284M | 177% |
| I284N | >500% |
| I284D | 214% |
| I284Q | 271% |
| I284S | 294% |
| I284T | 186% |
| D295S | 350% |
| D295N | 440% |
| D295E | 215% |
| D295G | 229% |

*positions being defined with reference to SEQ ID NO: 2

Example 4: Galactolipase to TAG-Lipase Activity Ratio at pH 8.0 of Variants According to the Disclosure Galactolipase to TAG-lipase activity ratio of variants as compared to the reference polypeptide was determined using the enzymes obtained in Example 2. This ratio was determined as described herein under Materials and Methods above (applying Assay 2B, Assay 3B, and "Exemplary determination and calculation of galactolipase to TAG-lipase activity ratio of variant #"). The results are listed in Table 3.

TABLE 3

Galactolipase to TAG-lipase activity ratio at pH 8.0 of variants according to the disclosure compared to the reference polypeptide. The galactolipase to TAG-lipase activity ratio of the reference polypeptide (polypeptide having an amino acid sequence as set out in amino acids 34 to 304 of SEQ ID NO: 2), was set at 100%. In the table normalised % are listed. A galactolipase to TAG-lipase activity ratio of more than 100% shows that the variant has an increased galactolipase activity compared to the reference polypeptide

| Amino Acid Change* | galactolipase to TAG-lipase activity ratio at pH 8.0 (%) |
|---|---|
| I113L | 122% |
| I113T | 151% |
| I113H | 273% |
| I113R | 247% |
| H138S | 128% |
| F141Y | 143% |
| F141M | 125% |
| V179L | 116% |
| V179S | >500% |
| V179M | 137% |
| L282R | 484% |
| L282E | 234% |
| L282S | >500% |
| I284M | 124% |
| I284P | 142% |
| I284N | 236% |
| I284D | >500% |
| I284E | 132% |
| I284Q | >500% |
| I284A | 140% |
| I284S | 174% |
| I284T | 138% |
| A286L | >500% |

TABLE 3-continued

Galactolipase to TAG-lipase activity ratio at pH 8.0 of variants according to the disclosure compared to the reference polypeptide. The galactolipase to TAG-lipase activity ratio of the reference polypeptide (polypeptide having an amino acid sequence as set out in amino acids 34 to 304 of SEQ ID NO: 2), was set at 100%. In the table normalised % are listed. A galactolipase to TAG-lipase activity ratio of more than 100% shows that the variant has an increased galactolipase activity compared to the reference polypeptide

| Amino Acid Change* | galactolipase to TAG-lipase activity ratio at pH 8.0 (%) |
|---|---|
| D295S | 231% |
| D295N | 251% |
| D295E | 139% |
| D295G | 174% |

*positions being defined with reference to SEQ ID NO: 2

Example 5: Phospholipase to TAG-Lipase Activity Ratio at pH 5.5 of Variants According to the Disclosure Phospholipase to TAG-lipase activity ratio of variants as compared to the reference polypeptide was determined using the enzymes obtained in Example 2. This ratio was determined as described herein under Materials and Methods above (applying Assay 1A, Assay 3A, and "Exemplary determination and calculation of galactolipase to TAG-lipase activity ratio of variant #"). The results are listed in Table 4.

TABLE 4

Phospholipase to TAG-lipase activity at pH 5.5 of variants according to the disclosure compared to the reference polypeptide. The phospholipase to TAG-lipase activity of the reference polypeptide (polypeptide having an amino acid sequence as set out in amino acids 34 to 304 of SEQ ID NO: 2), was set at 100%. In the table normalised % are listed. A phospholipase to TAG-lipase activity of more than 100% shows that the variant has an increased phospholipase activity compared to the reference polypeptide.

| Amino Acid Change* | phospholipase to TAG-lipase activity ratio at pH 5.5 (%) |
|---|---|
| I113N | 216% |
| I113T | 344% |
| I113H | 481% |
| I113R | 296% |
| F141Y | 268% |
| V179S | 179% |
| V179M | 137% |
| L282F | 122% |
| L282T | >500% |
| L282R | 149% |
| L282E | 117% |
| L282N | 116% |
| L282S | 150% |
| I284M | 149% |
| I284N | >500% |
| I284D | 390% |
| I284E | 171% |
| I284Q | >500% |
| I284S | 372% |
| I284T | 246% |
| D295S | 128% |

TABLE 4-continued

Phospholipase to TAG-lipase activity at pH 5.5 of variants according to the disclosure compared to the reference polypeptide. The phospholipase to TAG-lipase activity of the reference polypeptide (polypeptide having an amino acid sequence as set out in amino acids 34 to 304 of SEQ ID NO: 2), was set at 100%. In the table normalised % are listed. A phospholipase to TAG-lipase activity of more than 100% shows that the variant has an increased phospholipase activity compared to the reference polypeptide.

| Amino Acid Change* | phospholipase to TAG-lipase activity ratio at pH 5.5 (%) |
|---|---|
| D295N | 135% |
| D295G | 283% |

*positions being defined with reference to SEQ ID NO: 2

Example 6: Phospholipase to TAG-Lipase Activity Ratio at pH 8.0 of Variants According to the Disclosure Phospholipase to TAG-lipase activity ratio of variants as compared to the reference polypeptide was determined using the enzymes obtained in Example 2. This ratio was determined as described herein under Materials and Methods above (applying Assay 1B, Assay 3B, and "Exemplary determination and calculation of galactolipase to TAG-lipase activity ratio of variant #"). The results are listed in Table 5.

TABLE 5

Phospholipase to TAG-lipase activity at pH 8.0 of variants according to the disclosure compared to the reference polypeptide. The phospholipase to TAG-lipase activity of the reference polypeptide (polypeptide having an amino acid sequence as set out in amino acids 34 to 304 of SEQ ID NO: 2), was set at 100%. In the table normalised % are listed. A phospholipase to TAG-lipase activity of more than 100% shows that the variant has an increased phospholipase activity compared to the reference polypeptide.

| Amino Acid Change* | Phospholipase to TAG-lipase activity ratio at pH 8.0 (%) |
|---|---|
| I113L | 152% |
| I113T | 294% |
| I113H | >500% |
| I113R | >500% |
| L122M | 122% |
| L122A | 106% |
| H138E | 335% |
| F141Y | 171% |
| F141M | 156% |
| V179L | 113% |
| V179S | >500% |
| V179M | 126% |
| L282R | >500% |
| L282E | >500% |
| L282S | >500% |
| I284P | 132% |
| I284N | 242% |
| I284D | >500% |
| I284E | >500% |
| I284Q | >500% |
| I284A | 128% |
| I284S | 230% |
| I284T | 138% |
| A286L | 371% |
| D295S | 125% |
| D295N | 106% |
| D295G | 254% |

*positions being defined with reference to SEQ ID NO: 2

The invention claimed is:

1. A variant polypeptide having lipolytic activity, wherein the variant has an amino acid sequence which, when aligned with the amino acid sequence as set out in amino acid residues 34 to 304 of SEQ ID NO:2, comprises at least one substitution of an amino acid residue at a position corresponding to any of the positions 122, 138, 141, 282, 284, 286, 295,
said positions being defined with reference to SEQ ID NO:2,
and wherein said variant has at least 85% identity with the mature polypeptide having lipolytic activity as set out in SEQ ID NO:2.

2. The variant according to according to claim 1, wherein the variant has one or more altered properties as compared with a reference polypeptide having lipolytic activity.

3. The variant polypeptide according to claim 1, wherein the variant has an amino acid sequence which, when aligned with the amino acid sequence as set out in SEQ ID NO:2, comprises one or more of the amino acid substitutions selected from L122A; L122M; H138E; H138S; F141M; F141Y; L282E; L282F; L282K; L282M; L282N; L282R; L282S; L282T; I284A; I284D; I284E; I284M; I284N; I284P; I284Q; I284S; I284T; A286L; D295E; D295G; D295N; and D295S.

4. The variant according to according to claim 2, wherein the altered property is an increased ratio of the activity on polar lipids: activity on non-polar lipids as compared to the reference polypeptide having lipolytic activity measured under the same conditions.

5. A nucleic acid sequence encoding the variant polypeptide according to claim 1.

6. A nucleic acid construct comprising the nucleic acid sequence of claim 5 operably linked to one or more control sequences capable of directing the expression of a lipolytic enzyme in a suitable expression host.

7. A recombinant host cell comprising a recombinant expression vector comprising the nucleic acid construct of claim 6.

8. A method for producing the lipolytic polypeptide variant according to claim 1 comprising cultivating a host cell comprising a recombinant expression vector comprising a nucleic acid sequence encoding the lipolytic polypeptide variant, operably linked to one or more control sequences capable of directing the expression of a lipolytic polypeptide variant, under conditions conducive to production of the lipolytic enzyme variant and recovering the lipolytic enzyme variant.

9. A composition comprising the variant polypeptide according to claim 1 and one or more components selected from the group consisting of milk powder, gluten, granulated fat, an additional enzyme, an amino acid, a salt, an oxidant, a reducing agent, an emulsifier, sodium stearoyl lactylate, calcium stearoyl lactylate, polyglycerol esters of fatty acids and diacetyl tartaric acid esters of mono- and diglycerides, a gum, a flavour, an acid, a starch, a modified starch, a humectant and a preservative.

10. A dough comprising the variant polypeptide according to claim 1.

11. A process for the production of a dough, comprising of combining an effective amount of the variant polypeptide according to claim 1 with at least one dough ingredient.

12. A process for the production of a baked product, which method comprises baking the dough according to claim 10.

13. A dough comprising the composition according to claim 9.

14. A process for the production of a dough, comprising of combining an effective amount of the variant polypeptide obtained by the method-according to claim 8 with at least one dough ingredient.

15. A process for the production of a dough, comprising of combining an effective amount of the composition according to claim 9 with at least one dough ingredient.

16. A process for the production of a baked product, which method comprises baking the dough according to claim 13.

* * * * *

SEQUENCE LISTING

<160> NUMBER OF SEQ ID NOS: 7

<210> SEQ ID NO 1
<211> LENGTH: 1038
<212> TYPE: DNA
<213> ORGANISM: Artificial sequence
<220> FEATURE:
<223> OTHER INFORMATION: DNA lipolytic enzyme gene

<400> SEQUENCE: 1

```
atgcttctcc tctccctcct ctccattgtc accctcgctg ttgcttctcc tctgtccgtt      60
gaggagtacg ccaaggccct cgaggagcgt gccgtcaccg tctcctcctc cgagctcaac     120
aacttcaagt tctacatcca gcacggtgct gctgcctact gcaactccga gactgctgct     180
ggtgccaacg tcacctgcac tggcaacgcc tgccccgaga ttgaggccaa cggtgtcacc     240
gttgttgcct ccttcactgg taccaagact ggtatcggtg gctacgtctc caccgacaac     300
accaacaagg agatcgtcct tctttccgt ggcagcatca acatccgcaa ctggctgacc      360
aacctggact cggccagga tgactgctct ctgacctccg gctgcggtgt ccactccggt      420
ttccagcgtg cctgggagga gattgccgac aacctgaccg ctgctgttgc caaggccaag     480
actgccaacc ccgactacaa ggttgttgcc actggccact ccctgggtgg tgctgttgcc     540
accctggctg tgccaacct ccgtgctgct ggtaccccc tcgacatcta cacctacggc       600
tctccccgtg tcggcaacgc cgagcttgct gagttcatct ccaaccagac tggtggtgag     660
ttccgtgtca cccacggtga tgaccccgtc cccgtcttc tcctctgat cttcggctac       720
cgccacacct cccccgagta ctggctcgat ggcagcggtg gtgacaagat caactacacc     780
atcaacgaca tcaaggtctg cgagggtgct gccaacctgc agtgcaacgg tgtacccctg     840
ggtctcgaca ttgctgctca cctgcactac ttccaggcca ctgatgcctg caacgccggt     900
ggtttcagct ggcgccgcta ccgctctgct gagagcgttg acaagcgtgc caccatgact     960
gatgctgagc tcgagaagaa gctcaacagc tacgtgcaga tggacaagga gtacgtcaag    1020
aacaaccagg ctcgctcc                                                  1038
```

<210> SEQ ID NO 2
<211> LENGTH: 346
<212> TYPE: PRT
<213> ORGANISM: Artificial sequence
<220> FEATURE:
<223> OTHER INFORMATION: Lipolytic enzyme protein

<400> SEQUENCE: 2

```
Met Leu Leu Leu Ser Leu Leu Ser Ile Val Thr Leu Ala Val Ala Ser
1               5                   10                  15

Pro Leu Ser Val Glu Glu Tyr Ala Lys Ala Leu Glu Glu Arg Ala Val
            20                  25                  30

Thr Val Ser Ser Ser Glu Leu Asn Asn Phe Lys Phe Tyr Ile Gln His
        35                  40                  45

Gly Ala Ala Ala Tyr Cys Asn Ser Glu Thr Ala Ala Gly Ala Asn Val
    50                  55                  60

Thr Cys Thr Gly Asn Ala Cys Pro Glu Ile Glu Ala Asn Gly Val Thr
65                  70                  75                  80

Val Val Ala Ser Phe Thr Gly Thr Lys Thr Gly Ile Gly Gly Tyr Val
                85                  90                  95

Ser Thr Asp Asn Thr Asn Lys Glu Ile Val Leu Ser Phe Arg Gly Ser
            100                 105                 110
```

Ile Asn Ile Arg Asn Trp Leu Thr Asn Leu Asp Phe Gly Gln Asp Asp
            115                 120                 125

Cys Ser Leu Thr Ser Gly Cys Gly Val His Ser Gly Phe Gln Arg Ala
    130                 135                 140

Trp Glu Glu Ile Ala Asp Asn Leu Thr Ala Ala Val Ala Lys Ala Lys
145                 150                 155                 160

Thr Ala Asn Pro Asp Tyr Lys Val Val Ala Thr Gly His Ser Leu Gly
                165                 170                 175

Gly Ala Val Ala Thr Leu Ala Gly Ala Asn Leu Arg Ala Ala Gly Thr
            180                 185                 190

Pro Leu Asp Ile Tyr Thr Tyr Gly Ser Pro Arg Val Gly Asn Ala Glu
        195                 200                 205

Leu Ala Glu Phe Ile Ser Asn Gln Thr Gly Gly Glu Phe Arg Val Thr
    210                 215                 220

His Gly Asp Asp Pro Val Pro Arg Leu Pro Pro Leu Ile Phe Gly Tyr
225                 230                 235                 240

Arg His Thr Ser Pro Glu Tyr Trp Leu Asp Gly Ser Gly Gly Asp Lys
                245                 250                 255

Ile Asn Tyr Thr Ile Asn Asp Ile Lys Val Cys Glu Gly Ala Ala Asn
            260                 265                 270

Leu Gln Cys Asn Gly Gly Thr Leu Gly Leu Asp Ile Ala Ala His Leu
        275                 280                 285

His Tyr Phe Gln Ala Thr Asp Ala Cys Asn Ala Gly Gly Phe Ser Trp
    290                 295                 300

Arg Arg Tyr Arg Ser Ala Glu Ser Val Asp Lys Arg Ala Thr Met Thr
305                 310                 315                 320

Asp Ala Glu Leu Glu Lys Lys Leu Asn Ser Tyr Val Gln Met Asp Lys
                325                 330                 335

Glu Tyr Val Lys Asn Asn Gln Ala Arg Ser
            340                 345

<210> SEQ ID NO 3
<211> LENGTH: 13
<212> TYPE: DNA
<213> ORGANISM: Artificial Sequence
<220> FEATURE:
<223> OTHER INFORMATION: Sets out a modified translational initiation
      sequence of the glucoamylase glaA promoter

<400> SEQUENCE: 3
caccgtcaaa atg                                                        13

<210> SEQ ID NO 4
<211> LENGTH: 686
<212> TYPE: PRT
<213> ORGANISM: Alicyclobacillus pohliae

<400> SEQUENCE: 4

Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr

```
            65                  70                  75                  80

Leu Ala Gly Thr Asp Asn Thr Gly Tyr His Gly Tyr Trp Thr Arg Asp
                    85                  90                  95

Phe Lys Gln Ile Glu Glu His Phe Gly Asn Trp Thr Thr Phe Asp Thr
                100                 105                 110

Leu Val Asn Asp Ala His Gln Asn Gly Ile Lys Val Ile Val Asp Phe
                115                 120                 125

Val Pro Asn His Ser Thr Pro Phe Lys Ala Asn Asp Ser Thr Phe Ala
130                 135                 140

Glu Gly Gly Ala Leu Tyr Asp Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
                180                 185                 190

Gly Phe Ser Leu Ala Asp Leu Ser Gln Glu Asn Gly Thr Ile Ala Gln
                195                 200                 205

Tyr Leu Thr Asp Ala Ala Val Gln Leu Val Ala His Gly Ala Asp Gly
210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Ala Ala Asn His Leu Glu Lys Val Arg
                260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
                290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Thr Val
                325                 330                 335

Asn Ser Asn Lys Ala Asn Leu His Gln Ala Leu Ala Phe Ile Leu Thr
                340                 345                 350

Ser Arg Gly Thr Pro Ser Ile Tyr Tyr Gly Thr Glu Gln Tyr Met Ala
                355                 360                 365

Gly Gly Asn Asp Pro Tyr Asn Arg Gly Met Met Pro Ala Phe Asp Thr
                370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
                420                 425                 430

Val Ala Ile Asn Arg Asn Thr Gln Ser Ser Tyr Ser Ile Ser Gly Leu
                435                 440                 445

Gln Thr Ala Leu Pro Asn Gly Asn Tyr Ala Asp Tyr Leu Ser Gly Leu
450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495
```

```
Ser Ala Pro Gln Ile Gly Ser Val Ala Pro Asn Met Gly Ile Pro Gly
            500                 505                 510

Asn Val Thr Ile Asp Gly Lys Gly Phe Gly Thr Thr Gln Gly Thr
            515                 520                 525

Val Thr Phe Gly Gly Val Thr Ala Thr Val Lys Ser Trp Thr Ser Asn
    530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
            580                 585                 590

Pro Thr Asn Leu Gly Asp Lys Ile Tyr Leu Thr Gly Asn Ile Pro Glu
            595                 600                 605

Leu Gly Asn Trp Ser Thr Asp Thr Ser Gly Ala Val Asn Asn Ala Gln
    610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
            660                 665                 670

Pro Thr Gly Ala Thr Gly Asn Ile Thr Val Thr Trp Gln Asn
            675                 680                 685

<210> SEQ ID NO 5
<211> LENGTH: 686
<212> TYPE: PRT
<213> ORGANISM: Bacillus stearothermophilus

<400> SEQUENCE: 5

Ser Ser Ser Ala Ser Val Lys Gly Asp Val Ile Tyr Gln Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
```

```
                180             185             190
Gly Phe Ser Leu Ala Asp Leu Ser Gln Glu Asn Gly Thr Ile Ala Gln
            195                 200                 205
Tyr Leu Thr Asp Ala Ala Val Gln Leu Val Ala His Gly Ala Asp Gly
        210                 215                 220
Leu Arg Ile Asp Ala Val Lys His Phe Asn Ser Gly Phe Ser Lys Ser
225                 230                 235                 240
Leu Ala Asp Lys Leu Tyr Gln Lys Lys Asp Ile Phe Leu Val Gly Glu
                245                 250                 255
Trp Tyr Gly Asp Asp Pro Gly Thr Ala Asn His Leu Glu Lys Val Arg
            260                 265                 270
Tyr Ala Asn Asn Ser Gly Val Asn Val Leu Asp Phe Asp Leu Asn Thr
        275                 280                 285
Val Ile Arg Asn Val Phe Gly Thr Phe Thr Gln Thr Met Tyr Asp Leu
        290                 295                 300
Asn Asn Met Val Asn Gln Thr Gly Asn Glu Tyr Lys Tyr Lys Glu Asn
305                 310                 315                 320
Leu Ile Thr Phe Ile Asp Asn His Asp Met Ser Arg Phe Leu Ser Val
                325                 330                 335
Asn Ser Asn Lys Ala Asn Leu His Gln Ala Leu Ala Phe Ile Leu Thr
            340                 345                 350
Ser Arg Gly Thr Pro Ser Ile Tyr Tyr Gly Thr Glu Gln Tyr Met Ala
        355                 360                 365
Gly Gly Asn Asp Pro Tyr Asn Arg Gly Met Met Pro Ala Phe Asp Thr
    370                 375                 380
Thr Thr Thr Ala Phe Lys Glu Val Ser Thr Leu Ala Gly Leu Arg Arg
385                 390                 395                 400
Asn Asn Ala Ala Ile Gln Tyr Gly Thr Thr Thr Gln Arg Trp Ile Asn
                405                 410                 415
Asn Asp Val Tyr Ile Tyr Glu Arg Lys Phe Phe Asn Asp Val Val Leu
            420                 425                 430
Val Ala Ile Asn Arg Asn Thr Gln Ser Ser Tyr Ser Ile Ser Gly Leu
        435                 440                 445
Gln Thr Ala Leu Pro Asn Gly Ser Tyr Ala Asp Tyr Leu Ser Gly Leu
    450                 455                 460
Leu Gly Gly Asn Gly Ile Ser Val Ser Asn Gly Ser Val Ala Ser Phe
465                 470                 475                 480
Thr Leu Ala Pro Gly Ala Val Ser Val Trp Gln Tyr Ser Thr Ser Ala
                485                 490                 495
Ser Ala Pro Gln Ile Gly Ser Val Ala Pro Asn Met Gly Ile Pro Gly
            500                 505                 510
Asn Val Val Thr Ile Asp Gly Lys Gly Phe Gly Thr Thr Gln Gly Thr
        515                 520                 525
Val Thr Phe Gly Gly Val Thr Ala Thr Val Lys Ser Trp Thr Ser Asn
    530                 535                 540
Arg Ile Glu Val Tyr Val Pro Asn Met Ala Ala Gly Leu Thr Asp Val
545                 550                 555                 560
Lys Val Thr Ala Gly Gly Val Ser Ser Asn Leu Tyr Ser Tyr Asn Ile
                565                 570                 575
Leu Ser Gly Thr Gln Thr Ser Val Val Phe Thr Val Lys Ser Ala Pro
            580                 585                 590
Pro Thr Asn Leu Gly Asp Lys Ile Tyr Leu Thr Gly Asn Ile Pro Glu
        595                 600                 605
```

Leu Gly Asn Trp Ser Thr Asp Thr Ser Gly Ala Val Asn Asn Ala Gln
        610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
                660                 665                 670

Pro Thr Gly Ala Thr Gly Asn Ile Thr Val Thr Trp Gln Asn
        675                 680                 685

<210> SEQ ID NO 6
<211> LENGTH: 429
<212> TYPE: PRT
<213> ORGANISM: Pseudomonas saccharophilia

<400> SEQUENCE: 6

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly

```
            290                 295                 300
Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
                340                 345                 350

Arg Thr Ala Gly Val Arg Ala Asp Ser Ala Ile Ser Phe His Ser Gly
                355                 360                 365

Tyr Ser Gly Leu Val Ala Thr Val Ser Gly Ser Gln Gln Thr Leu Val
                370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
                420                 425
```

<210> SEQ ID NO 7
<211> LENGTH: 429
<212> TYPE: PRT
<213> ORGANISM: Artificial Sequence
<220> FEATURE:
<223> OTHER INFORMATION: Synthetic polypeptide

<400> SEQUENCE: 7

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ser Thr Ile Ala Ala
                35                  40                  45

Asp Gly Phe Ser Ala Ile Trp Met Pro Val Pro Trp Arg Asp Phe Ser
            50                  55                  60

Ser Trp Thr Asp Gly Asp Lys Ser Gly Gly Gly Glu Gly Tyr Phe Trp
65              70                  75                  80

His Asp Phe Asn Lys Asn Gly Arg Tyr Gly Ser Asp Ala Gln Leu Arg
                85                  90                  95

Gln Ala Ala Gly Ala Leu Gly Ala Gly Val Lys Val Leu Tyr Asp
                100                 105                 110

Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
                195                 200                 205

Asp Ser Ala Asp Ser Ser Phe Cys Val Gly Glu Leu Trp Lys Glu Pro
            210                 215                 220

Ser Glu Tyr Pro Pro Trp Asp Trp Arg Asn Thr Ala Ser Trp Gln Gln
```

```
                225                 230                 235                 240
          Ile Ile Lys Asp Trp Ser Asp Arg Ala Lys Cys Pro Val Phe Asp Phe
                          245                 250                 255

Ala Leu Lys Glu Arg Met Gln Asn Gly Ser Val Ala Asp Trp Lys His
                          260                 265                 270

Gly Leu Asn Gly Asn Pro Asp Pro Arg Trp Arg Glu Val Ala Val Thr
                      275                 280                 285

Phe Val Asp Asn His Asp Thr Gly Tyr Ser Pro Gly Gln Asn Gly Gly
                      290                 295                 300

Gln His Lys Trp Pro Leu Gln Asp Gly Leu Ile Arg Gln Ala Tyr Ala
          305                 310                 315                 320

Tyr Ile Leu Thr Ser Pro Gly Thr Pro Val Val Tyr Trp Pro His Met
                          325                 330                 335

Tyr Asp Trp Gly Tyr Gly Asp Phe Ile Arg Gln Leu Ile Gln Val Arg
                          340                 345                 350

Arg Thr Ala Gly Val Arg Ala Asp Ser Ala Ile Ser Phe His Ser Gly
                          355                 360                 365

Tyr Ser Gly Leu Val Ala Thr Val Ser Gly Ser Gln Gln Thr Leu Val
                      370                 375                 380

Val Ala Leu Asn Ser Asp Leu Ala Asn Pro Gly Gln Val Ala Ser Gly
          385                 390                 395                 400

Ser Phe Ser Glu Ala Val Asn Ala Ser Asn Gly Gln Val Arg Val Trp
                          405                 410                 415

Arg Ser Gly Ser Gly Asp Gly Gly Asn Asp Gly Gly
                          420                 425
```